(12) United States Patent
Nakashima et al.

(10) Patent No.: US 8,920,791 B2
(45) Date of Patent: Dec. 30, 2014

(54) ROOT CANAL FILLER AND DENTAL TISSUE REGENERATION METHOD

(75) Inventors: Misako Nakashima, Obu (JP); Koichiro Iohara, Obu (JP)

(73) Assignee: Japan Health Sciences Foundation, Tokyo (JP)

( * ) Notice: Subject to any disclaimer, the term of this patent is extended or adjusted under 35 U.S.C. 154(b) by 386 days.

(21) Appl. No.: 12/922,097

(22) PCT Filed: Mar. 12, 2009

(86) PCT No.: PCT/JP2009/055541
§ 371 (c)(1),
(2), (4) Date: Sep. 10, 2010

(87) PCT Pub. No.: WO2009/113733
PCT Pub. Date: Sep. 17, 2009

(65) Prior Publication Data
US 2011/0020310 A1  Jan. 27, 2011

(30) Foreign Application Priority Data
Mar. 12, 2008 (JP) ................................ 2008-063391

(51) Int. Cl.
| | |
|---|---|
| A61K 6/02 | (2006.01) |
| A61K 35/12 | (2006.01) |
| A61L 27/38 | (2006.01) |
| A61K 6/00 | (2006.01) |
| A61L 27/36 | (2006.01) |

(52) U.S. Cl.
CPC .......... A61L 27/3834 (2013.01); A61K 6/0032 (2013.01); A61L 27/3633 (2013.01); A61L 27/3865 (2013.01); A61L 2400/06 (2013.01); A61L 2430/12 (2013.01)
USPC ...................................................... 424/93.7

(58) Field of Classification Search
CPC ............... A61K 38/193; A61K 6/0032; A61L 2430/12; A61L 27/3633; A61L 27/3834; A61L 27/3865; C12N 5/0664
USPC ...................................................... 424/93.7
See application file for complete search history.

(56) References Cited

U.S. PATENT DOCUMENTS

| | | | |
|---|---|---|---|
| 2003/0113812 A1 | 6/2003 | Hemperly | |
| 2005/0079470 A1* | 4/2005 | Rutherford et al. | ........... 433/226 |
| 2005/0282116 A1 | 12/2005 | Kusano | |
| 2007/0248933 A1 | 10/2007 | Rutherford et al. | |
| 2009/0148486 A1 | 6/2009 | Lu et al. | |
| 2010/0196854 A1* | 8/2010 | Shi et al. | ........... 433/175 |
| 2010/0203481 A1 | 8/2010 | Murray et al. | |
| 2011/0002895 A1 | 1/2011 | Ueda et al. | |
| 2011/0020310 A1 | 1/2011 | Nakashima et al. | |
| 2011/0044960 A1 | 2/2011 | Nakashima et al. | |

FOREIGN PATENT DOCUMENTS

| | | |
|---|---|---|
| EP | 2286829 A1 | 2/2011 |
| JP | 6-256132 A | 9/1994 |
| JP | 2002-29911 A | 1/2002 |
| JP | 2002-363084 A | 12/2002 |
| JP | 2004-067630 A | 3/2004 |
| JP | 2005-263681 A | 9/2005 |
| JP | 2006-1910 A | 1/2006 |
| JP | 2006-211957 A | 8/2006 |
| WO | WO 01/63287 A1 | 8/2001 |
| WO | 2004/094588 A2 | 11/2004 |
| WO | WO 2005/034789 A2 | 4/2005 |
| WO | WO 2006032075 A1 * | 3/2006 ............... C12N 5/06 |
| WO | 2006/116530 A2 | 11/2006 |
| WO | 2009/078971 A1 | 6/2009 |
| WO | WO 2009/072527 A1 | 6/2009 |
| WO | WO 2009/113733 A1 | 9/2009 |
| WO | 2009/125859 A1 | 10/2009 |

OTHER PUBLICATIONS

Iohara et al. A Novel Stem Cell Source for Vasculogenesis in Ischemia: Subfraction of Side Population Cells from Dental Pulp. Stem Cells 2008;26:2408-2418.*
Kan-Ichi Nakagawa, et al., "Hydroxyapatite no Konkan Jutenzai to shite no Oya kachi ni Kansuru Jikken Byorigakuteki Kenkyu (Dai 1 Po)", Histo-pathological Studies of Synthetic Hydroxyapatitie Applied as Root Canal Filling Materials to Apical Wonds of Dog Teeth, The Japanese Society of Conservative Dentistry, vol. 27 No. 1, 1984, pp. 190-199, Received for Publication: Dec. 28, 1983.
Misako Nakashima, et al., The Application of Tissue Engineering to Regeneration of Pulp and Dentin in Endodontics, Journal of endodontics, vol. 31, No. 10, Oct. 2005, pp. 711-718.
Misako Nakashima, et al., Gene Therapy for Dentin Regeneration with Bone Morphogenetic Proteins, Current Gene Therapy, 2006 vol. 6, No. 5, pp. 551-560, Accepted Aug. 1, 2006.
Weibo Zhang, et al., The performance of human dental pulp stem cells on differenct three-dimensional scaffold materials, Biomaterials 27, vol. 27, No. 33, pp. 5658-5668, accepted Jul. 11, 2006.
A.J. Sloan, et al., Stem cells and the dental pulp: potential roles in dentine regeneration and repair, Oral Diseases, 2007, vol. 13, No. 2, pp. 151-157, accepted Sep. 21, 2006.
Misako Nakashima, Tissue Engineering of Teeth, Handbook of Biomineralization, 2007, vol. 3, Medical and Clinical Aspects, pp. 265-281.
Koichiro Iohara, et al. Side Population Cells Isolated from Porcine Dental Pulp Tissue with Self-Renewal and Multipotency for Dentinogenesis, Chondrogenesis, Adipogenesis, and Neurogenesis, National Institute of for Longevity Sciences Labrary on Jan. 23, 2007, Alpha Med Press, pp. 2492-2504.

(Continued)

Primary Examiner — Taeyoon Kim
(74) Attorney, Agent, or Firm — Knobbe, Martens, Olson & Bear, LLP

(57) ABSTRACT

Provided is a novel and creative dental tissue regeneration method for regenerating dental tissue after pulpectomy or the enlargement and cleaning of an infected root canal. After pulpectomy or the enlargement and cleaning of an infected root canal, a root canal filler (200) having an extracellular matrix (210) containing the cells (220) enriched for dental pulp stem cells, is inserted into the apical side of the root canal of a target tooth (100). The cells including dental pulp stem cells include at least one of the following: dental pulp SP cells, CD31-negative and CD146-negative cells, CD24-positive cells, CD105-positive cells, and CD150-positive cells. For instance, dental pulp SP cells are CD31⁻ and CD146⁻ negative. Even if pulpitis due to deep caries occurs, appropriate dental pulp regeneration and recovery of dental pulp function are possible.

8 Claims, 39 Drawing Sheets

(56) References Cited

OTHER PUBLICATIONS

Wim Laureys, et al., Revascularization after cryopreservation and autotransplantation of immature and mature apicoectomized teeth, American Jounal of Orthodontics and Dentofacial Orthopedics, vol. 119, No. 4, Apr. 2001, pp. 346-352.

Masako Nakashim, et al., The application of bone morphogenetic proteins to dental tissue engineering, Nature Biotechnology, vol. 21, No. 9, Sep. 2003, pp. 1025-1032.

Amano, K. et al. 2007 "MMPs regulate wound healing process in rat dental pulp" *Japanese Society of conservative Dentistry Magazine*, pp. 35.

Boukpessi et al. "The effect of stromelysin-1 (MMP-3) on non-collagenous extracellular matrix proteins of demineralized dentin and the adhesive properties of restorative resins." Aug. 2008, *Biomaterials*, 29, 4367-4373).

Corti, S. et al. 2005 "Multipotentiality, homing properties, and pyramidal neurogenesis of CNS-derived $LeX(ssea-1)^+/CXCR4^+$ stem cells" *The FASEB Journal* 19: 1860-1862.

Huang, G.T.-J, et al, 2009: "Stem/Progenitor Cell-Mediated De Novo Regeneration of Dental Pulp with Newly Deposited Continuous Layer of Dentin in an In Vivo Model", *Tissue Engineering*, 16(2): 605-615.

Iohara, K. et al., 2007 "CD31 negative SP cells derived from dental pulp accelerate vascularization and pulp regeneration" *Japanese Society of conservative Dentistry Magazine*, p. 106.

Iohara, K. et al. 2009 "Regeneration of dental pulp after pulpotomy by transplantation of CD31-/CD146− side population cells from a canine tooth" Regenerative Medicine 4: 377-385.

Kawanishi, H.N. et al. 2004 "Effects of an inducible nitric oxide synthase inhibitor on experimentally induced rat pulpitis" *European Journal of Oral Science*; 112; pp. 332-327.

Koblas, T. et al. 2007 "Isolation and Characterization of Human CXCR4-Positive Pancreatic Cells" *Folia Biol (Praha)* 53: 13-22.

Kucia, M et al. 2007 "Morphological and molecular characterization of novel population of $CXCR4^+$ $SSEA-4^+$ $Oct-4^+$ very small embryonic-like cells purified from human cord blood—preliminary report" *Leukemia* 21: 297-303.

Moriguchi, M. et al. 1998 "Immunocytochemistry of proteoglycan in dentin and odontoblasts" *Kaibogaku Zasshi—Acta Anatomica Nipponica* 73: 239-245.

Nakagawa, K.-I. et al. 1984 "Histo-pathological Studies of Synthetic Hydroxyapatite Applied as Root Canal Filling Materials to Apical Wounds of Dog Teeth (Part 1)" *The Japanese Journal of conservative Dentistry* 27: 190-199.

Nakao and Tsuji, "Dental regenerative therapy: Stem cell transplantation and bioengineered tooth replacement", (2008), *Japanese Dental Science Review*, 44, 70-75.

Nakashima, M, et al, 2009: "Human dental pulp stems with highly angiogenic and neurogenic potential for possible use in pulp regenartion", *Cytokine & Growth Factor Reviews*, 20(6): 435-440.

Soukup, T, et al, 2006: "Biological properties and flow cytometric analysis of human dental pulp stem cells", *Cytotherapy, Isis Medical Media*, 8(2): 3.

Tsutsui, T. et al., 2005 "Acceleration of calcification by co-culture of epithelial cells derived from human gum and fibroblasts, and epithelial cells derived from human gum and dental pulp cells" *Journal of Oral Biosciences*; 47, p. 155, 324 2P.

Tsutsui, T. et al.,2007 "Calcification under co-culture of pithelial cells and mesenchymal cells" *Oral Tissue Culture Association Magazine*, 16 (1), pp. 11-12.

Yang et al. "The Design of Scaffolds for Use in Tissue Engineering. Part I, Traditional Factors." 2001, *Tissue Engineering*, 7(6), 679-689.

Yoshiyama, M., et al., "Seeking a New Caries Treatment: New Conversion from Restoration to Dentin Regeneration" Japan Association for Dental Science Magazine, vol. 22, 2003, pp. 76-80.

Murray et al., "Regenerative Endodontics: A Review of Current Status and a Call for Action", Journal of Endodontics, Lippincott Williams & Wilkins, Philadelphia, PA, US, vol. 33, No. 4, Mar. 16, 2007, pp. 377-390.

Nakashima, "Tissue engineering of teeth, Handbook of Biomineralization", Medical and Clinical Aspects, vol. 3, 2007, pp. 265-281.

Eric L Gotlieb et al., "An Ultrastructural Investigation of Tissue-Engineered Pulp Constructs Implanted Within Endodontically Treated Teeth", Journal of the American Dental Association, American Dental Association, US, vol. 139, No. 4, Apr. 1, 2008, pp. 457-465.

Extended European Search Report dated Mar. 26, 2013 of corresponding European Patent Application No. 09718864.3—12 pages.

Iohara, K. et al., Field C, Subject No. KHC3362, FY2006 Rep011 "Development of New Pulpectomy Therapy by Regenerating Dental Pulp and Dentine, Aiming at Life Prolongation of Teeth for Aging Societies" Jul. 31, 2007, pp. 162-166.

\* cited by examiner

500 μm

500 μm

500 μm

100 μm

100 μm

500 μm

500 μm

50 μm

100 μm

50 μm

50 μm

500 μ m

500 μm

500 μm

500 μm

100 μm

100 μm

20 μm

50 μm

500 μ m

500 μm

500 μm

500 μm

500 μm

100 μm

50 μm

50 μm

ROOT CANAL FILLER AND DENTAL TISSUE REGENERATION METHOD

This application is the U.S. National Phase under 35. U.S.C. §371 of International Application PCT/JP2009/055541, filed Mar. 12, 2009, which claims priority to Japanese Patent Application No. 2008-063391, filed Mar. 12, 2008 The International Application was published under PCT Article 21(2) in a language other than English.

TECHNICAL FIELD

The present invention relates to a root canal filler and a dental tissue regeneration method by using the root canal filler.

BACKGROUND ART

When dental caries is deep enough to reach dental pulp, pulpectomy is usually performed for treatment of the caries. However, the dental pulp not only has a function to block external stimulus by reparative dentin formation, but also functions to inhibit further invasion of bacterial by sense and prevent tooth fracture caused by chewing a hard material with the sense of occlusion. In addition, the dental pulp can maintain protein and water in dentin by metabolism, and additionally keep the tensile strength and other properties of dentin. The dental pulp is also known to have an infection defense mechanism by immune system.

NiTi alloy rotary files are used popularly in endodontics, because of morphological complexity of the root canal. However, complete pulpectomy, enlargement of root canal and root canal filling are almost impossible. Thus, pulpectomy often leads to periapical periodontitis, and has high possibility of resultant loss of the tooth.

There is unmet need for development of a method to preserve the dental pulp as long as possible for longevity of teeth. Thus, technological development for a novel method for caries treatment is under progress to regenerate dentin and dental pulp by using triad of tooth regeneration: 1) morphogen (BMPs (bone morphogenetic proteins), etc.) 2) dental pulp stem cells, and 3) microenvironment (scaffold, extracellular matrix, etc.).

First, as described in Nonpatent Literature 1 and 2, there is, ex vivo cell therapy or gene therapy, to regenerate a large amount of dentin rapidly. In this method, BMP protein or BMP gene were introduced into dental pulp stem cells in vitro to induce their differentiation into odontoblasts in three-dimensional culture, and the differentiated odontoblasts were transplanted on the exposed pulp tissue.

As described in Nonpatent Literature 3, generation of a large number of human dental pulp stem cells, which does not cause transplant rejection, is now under progress for clinical application of the methods described above. And side population (SP) cells, which are highly enriched for stem cells, have been characterized by molecular biological methods.

When the dental pulp tissue is some kind of accidental exposure or reversible pulpitis, the dentin regeneration method described above would be effective. However when the tissue is irreversible pulpitis with pain, there is no choice but to perform pulpectomy.

In the case of autologous replantation in a human immature tooth with incomplete apical closure, it is known that the dental pulp is regenerated at high frequency after replantation. Additionally, the pulp regeneration is accompanied by mineralization in the pulp cavity and the root canal, root development and closure of apical dental foramen, thus preventing root fracture. Even if the dental pulp is necrotic, the remaining extracellular matrix may function, if there is no infection, as a scaffold for infiltration of blood vessels and cells.

The cells existing in the periapical tissue are still alive during replantation, and may migrate in the direction to the tooth crown and proliferate there in the root canal after replantation.

On the other hand, in the case of canine immature tooth, the dental pulp is regenerated similarly when the tooth is replanted even after complete removal of pulp tissue. There is a report on dental pulp regeneration even in the case of an immature tooth with periapical lesion. In this report, the root canal is cleaned, disinfected thoroughly, applied with three different kinds of mixture of antibacterial agents, and filled with blood clot to the cementodentinal junction. The cavity is further completely sealed with Mineral trioxide aggregate (MTA) and Cavit.

In addition, as described in Nonpatent Literature 4, it has been reported that, even in the case of canine healthy mature tooth, regeneration of dental pulp was observed, if the apical root is cut off to enlarge the apical foramen by apicoectomy followed by pulpectomy, and the tooth was replanted and filled with blood clot in the root canal.

However, most of the reports on pulp regeneration in the emptied root canal are those in immature teeth. In the case of deep caries with pulpitis or periapical periodontitis in mature teeth with complete apical closure, no method nor root canal filler for dental tissue regeneration have been developed yet.

Patent Documents 1 and 2 describe root canal fillers made of synthetic materials. However, in these cases, the root canal filler may be separated from the dentinal wall or ruptured after root canal filling. In addition, these root canal fillers may cause periapical periodontitis in several years.

CITATION LIST

Patent Document

PATENT DOCUMENT 1: Japanese Patent Publication No. 2006-001910
PATENT DOCUMENT 2: Japanese Patent Publication No. 2002-029911

Non-Patent Document

NON-PATENT DOCUMENT 1: Nakashima and Reddi, 2003; (PMID 12949568 doi 10.1038/nbt864)
NON-PATENT DOCUMENT 2: Nakashima and Akamine, 2006 (PMID:16186748)
NON-PATENT DOCUMENT 3: Iohara et al., 2006 (PMID: 16873765 doi: 10.1634/stemcells, 2006-0161)
NON-PATENT DOCUMENT 4: Laureys et al., 2001 (PMID: 11298308 doi: 10.1067/mod.2001.113259)

SUMMARY OF THE INVENTION

Technical Problem

An object of the present invention, which was made to solve the problems above, is to provide a novel and creative root canal filler for regeneration of dental tissue by filling a scaffold into the root canal of a mature tooth with complete apical closure after pulpectomy and a dental tissue regeneration method by using such a root canal filler.

Solution to the Problem

The dental tissue regeneration method of the first viewpoint of the present invention, which was made to achieve the object above, is characterized by regenerating dental tissue in a root canal. In this method, a root canal filler with an extracellular matrix containing the cells enriched for dental pulp stem cells were injected into the apical side of the root canal, after pulpectomy or after enlargement and cleaning of the root canal of infected root canal of periapical disease.

The cells including dental pulp stem cells may contain at least one of dental pulp SP cells, CD31-negative/CD146-negative cells, CD24-positive cells, CD105-positive cells and, CD150-positive cells.

The dental pulp SP cells may be CD31-negative/CD146-negative, CD24-positive, CD105-positive or CD150-positive.

The root canal filler preferably has the cells enriched for dental pulp stem cells injected in the apical side of the root canal and has a chemotactic (migration) factor containing at least one of cell chemotactic factor, cell growth factor and neurotrophic factor injected in the tooth crown-side of the root canal.

The cell chemotactic (migration) factor may be at least one of SDF1, VEGF, GCSF, MMP3, Slit and GMCSF.

The cell growth factor may be at least one of bFGF and PDGF.

The neurotrophic factor may be at least one of GDNF, BDNF and NGF.

The extracellular matrix may be made of a biocompatible material containing at least one of collagen, synthetic proteoglycans, gelatin, hydrogel, fibrin, phosphophorin, heparan sulfate, heparin, laminin, fibronectin, alginic acid, hyaluronic acid, chitin, PLA, PLGA, PEG, PGA, PDLLA, PCL, hydroxyapatite, β-TCP, calcium carbonate, titanium and gold.

The width of the root canal in the apical area may be adjusted to a particular size by enlargement of the root canal before insertion of the root canal filler into the apical side of the root canal.

The content of the dental pulp stem cells in the extracellular matrix having the attached cells including dental pulp stem cells may be $1 \times 10^3$ cell/µl or more and $1 \times 10^6$ cell/µl or less.

The root canal filler of the second viewpoint of the present invention, which was made to achieve the object above, is characterized by having an extracellular matrix containing the cells enriched for dental pulp stem cells.

The cells including dental pulp stem cells may contain at least one of dental pulp SP cells, CD31-negative/CD146-negative cells, CD24-positive cells, CD105-positive cells and CD150-positive cells.

The dental pulp SP cells may be CD31-negative/CD146-negative, CD24-positive, CD105-positive, or CD150-positive.

The extracellular matrix may be made of a biocompatible material containing at least one of collagen, synthetic proteoglycans, gelatin, hydrogel, fibrin, phosphophorin, heparan sulfate, heparin, laminin, fibronectin, alginic acid, hyaluronic acid, chitin, PLA, PLGA, PEG, PGA, PDLLA, PCL, hydroxyapatite, β-TCP, calcium carbonate, titanium and gold.

The content of the dental pulp stem cells in the extracellular matrix having the attached cells enriched for dental pulp stem cells may be $1 \times 10^3$ cell/µl or more and $1 \times 10^6$ cell/µl or less.

Advantages of the Invention

It was possible to regenerate dental tissue by inserting the root canal filler according to the present invention into the root canal after pulpectomy or enlargement and cleaning of the root canal of the infected root canal, even in the case of deep caries with pulpitis or periapical disease with mature teeth with complete apical closure. The root canal filler according to the present invention accelerates regeneration of blood vessel and nerve and regeneration of dental pulp and restoration of dental pulp function, by proliferation of dental pulp cells. In addition, application of a morphogen such as BMP or a growth/differentiation factor on tooth-crown dental pulp resulted in accelerated differentiation of dental pulp cells into odontoblasts and lead to blockage of the tooth crown region with dentin. Further, the apical dental foramen was sealed by addition of tooth cementum.

DESCRIPTION OF EMBODIMENTS

Hereinafter, favorable embodiments of the present invention will be described specifically with reference to attached figures.

(Embodiment 1)

The invention in the present embodiment relates to a dental tissue regeneration method for regeneration of dental tissue in root canal, characterized by injecting an extracellular matrix containing the cells enriched for dental pulp stem cells into the apical side of the root canal after pulpectomy or enlargement and cleaning of an infected root canal. The dental tissues to be regenerated are, for example, blood vessel, nerve, dental pulp, dentin and others in root canal. In the invention in the present embodiment after pulpectomy or enlargement and cleaning of an infected root canal, the dental pulp is removed and disinfected; the apical portion of the root is cut out open (apicoectomized); and a root canal filler is transplanted. In the invention in the present embodiment, a synthetic filler or blood clot is not transplanted into the disinfected hollow root canal, but a scaffold superior in biocompatibility without causing adverse effects and in low immunogenicity with cells including dental pulp stem cells, which mimics dental pulp tissue, is used. The root canal filler is preferably filled to ¼ to ⅔ of the apical part of the root canal, more preferably ⅓ of the apical part.

Figure 1A:
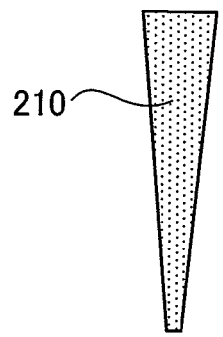
FIG. 1A is a schematic view illustrating an extracellular matrix.

Hereinafter, the dental tissue regeneration method in embodiment 1 will be described with reference to FIGS. 1A to 1K. As shown in FIG. 1A, an extracellular matrix 210 is prepared. The extracellular matrix 210 is the so-called scaffold, a matrix for cell attachment. The shape of the extracellular matrix 210 is preferable to be cylindrical or mostly conical in shape for easier filling into root canal. If the extracellular matrix 210 is gel, it is indefinite in shape.

The extracellular matrix 210 is preferably made of a biocompatible material containing at least one of the following substances: collagen, synthetic proteoglycans, gelatin, hydrogel, fibrin, phosphophorin, heparan sulfate, heparin, laminin, fibronectin, alginic acid, hyaluronic acid, chitin, PLA (polylactic acid), PLGA (lactic acid/glycolic acid copolymers), PEG (polyethylene glycol), PGA (polyglycol acid), PDLLA (poly-DL-lactic acid), PCL (polycaprolactone), hydroxyapatite, β-TCP, calcium carbonate, titanium and gold. The proteoglycans above are composite sugars consisting of proteins and sugar chains (glucosaminoglycans) covalent bound to each other. The extracellular matrix 210 for use may be a sponge-shaped three-dimensional structure made of a nanofiber having a number-average diameter of 1 nm to 1000 nm prepared with a polymer such as thermoplastic polymer. The void rate of such a three-dimensional structure is preferably 80% to 99.99%.

The collagen used as the extracellular matrix 210 is preferably a mixed collagen of type I and III collagens. The type I collagen is a basic collagen, which is fibrous. The type III collagen forms a fine network structure, called reticular fiber, different from the collagen fiber and provides a matrix for fixation of cells and others.

The rate of the type III collagen in the mixed collagen described above is preferably 30 wt % or more and 50 wt % or less. It is because the mixed collagen may not be solidified when the type III collagen rate is more than 50 wt %. Alternatively when the type III collagen rate is less than 30 wt %, the rate of the type I collagen increases, possibly leading to dentin regeneration, not to vascularization, as described below. The mixing rate of the type I and III collagens is most preferably 1:1.

Figure 1B:
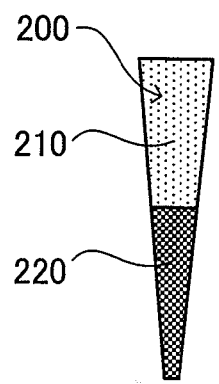
FIG. 1B is a schematic view explaining a root canal filler formed by attaching cells enriched for dental pulp stem cells on the extracellular matrix.

As shown in FIG. 1B, the root canal filler 200 is prepared by attaching cells 220 including dental pulp stem cells to the extracellular matrix 210. The cells 220 including dental pulp stem cells are attached to the apical part of the root canal of the root canal filler 200. In a typical example of the method of producing the root canal filler 200, 30 to 40 µl of mixed collagen (mixing rate of type I and III collagens: 1:1) is first absorbed and 20 to 30 µl of mixed collagen together with cells including dental pulp stem cells is then absorbed into the tip of Pipetman, to a total amount of 60 µl. Absorption, for example into the tip of Pipetman is preferable to be sufficiently slow so that no air bubble is generated. It is because, if air bubbles are formed in the root canal filler 200, the generated bubbles may inhibit migration of cells, inhibiting acceleration of the dental tissue regeneration. The internal diameter of the Pipetman tip is preferably smaller and, for example, a tip having a bottom internal diameter of 0.5 to 0.7 mm, such as H-010-96RS microcapillary tip from QSP, can be used.

Figure 1C:
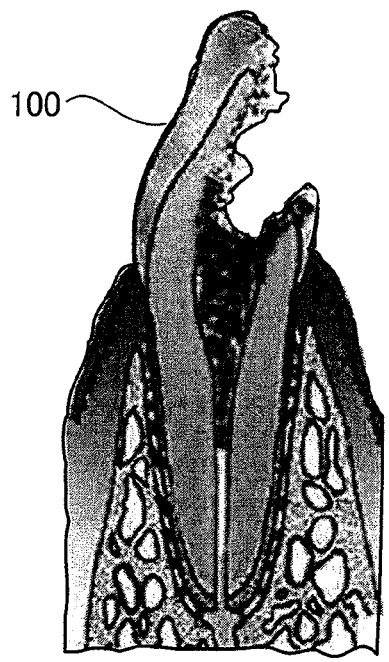
FIG. 1C is an explanatory view illustrating a targeted pulpitis.
Figure 1D:
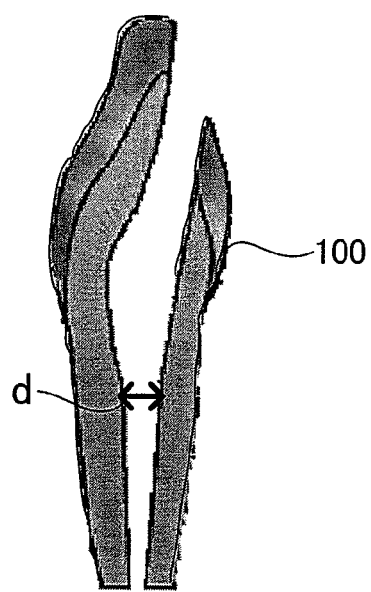
FIG. 1D is a schematic view explaining a tooth after pulpectomy and enlargement of the root canal.

As shown in FIG. 1C, for example, a tooth 100 with pulpitis is subjected to extracted in the dental tissue regeneration method in the present embodiment. As shown in FIG. 1D, the targeted tooth 100 is then subjected to pulpectomy. The targeted tooth 100 is a tooth in which microbial infection reaches the coronal pulp or the radicular pulp because of caries, pulpitis etc. Pulpectomy is an operation to remove the whole dental pulp present in the tooth.

After pulpectomy, it is desirable to adjust the size of the apical foramen to a particular width, by enlargement of the root canal of the targeted tooth 100. As will be described below, it is because it is easier to fill the root canal filler in fixing the root canal filler in the root canal after pulpectomy and blood vessel and nerve penetrate therein easily from the apical periodontal tissue, if the root canal is enlarged.

For example, as shown in FIG. 1D, the width d of the apical foramen, i.e., the diameter of root canal, is desirably 0.7 mm or more and 1.5 mm or less. When the width d of the root canal is less than 0.7 mm, blood vessel and nerve do not penetrate easily from the apical periodontal tissue, and it may be difficult to fill the root canal filler, while when the width d of the root canal is more than 1.5 mm, enlargement of the root canal may lead to application of a load more than needed on the targeted tooth 100, thus causing tooth fracture.

Figure 1E:
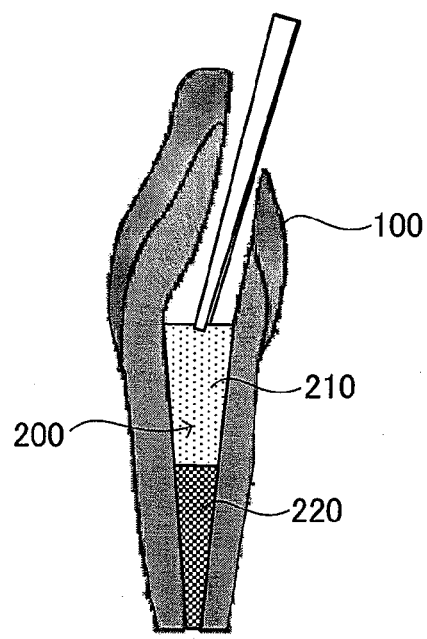
FIG. 1E is a schematic view explaining insertion of the root canal filler.

After pulpectomy of the targeted tooth 100, as shown in FIG. 1E, the root canal filler 200 is inserted into the apical side of the root canal for example with tweezers. The root canal filler 200 may be a biological root canal filler, because it contains biological materials such as dental pulp SP cells. When the extracellular matrix 210 is gel, it is injected for example with Pipetman or syringe, because it cannot be held with tweezers.

The cells including dental pulp stem cells may be the autologous cells extracted from the animal subjected to the treatment for dental tissue regeneration or the allogeneic cells extracted from an animal different from the animal subjected to the treatment for dental tissue regeneration.

The dental pulp stem cell is a dental pulp stem cell derived from permanent tooth or deciduous tooth. In particular, the dental pulp cells derived from human deciduous tooth contains $CD105^+$ cells in a greater amount, representing approximately 50%. (Human permanent tooth-derived $CD31^-$ SP cells contain $CD105^+$ cells, representing approximately 20%). The deciduous tooth-derived dental pulp cells has angiogenic potential in vitro and increase blood flow and accelerate vascularization after transplantation in hindlimb ischemic region, almost similarly to permanent tooth $CD105^+$ cells or SP cells. The deciduous tooth pulp cells contain $CD150^+$, representing 0.2%, which is higher compared with permanent tooth $CD31^-$ SP cells, representing 0.1%. In addition, the deciduous tooth pulp cells, even without fractionation, can be used for vascularization and dental pulp regeneration after pulpectomy. For example in the case of vascularization in hindlimb ischemic regions, human deciduous tooth-derived dental pulp cells have a vasculogenic potental 2.2 times higher than that of the human permanent tooth-derived dental pulp cells.

The cells including dental pulp stem cells preferably contain at least one of dental pulp SP cells, CD31-negative/CD146-negative cells, CD24-positive cells, CD105-positive cells and CD150-positive cells. For example, human dental pulp SP cells have high tissue regeneration potential such as vasculogenic potental. Specifically in the case of vascularization in hindlimb ischemic regions, the human dental pulp SP cells have a vasculogenic potental 1.2 times higher than that of the human deciduous tooth pulp cells. In addition, the human dental pulp SP cells have a vasculogenic potental 2.6 times higher than that of human permanent tooth pulp cells. Further, the cells have a vasculogenic potental 5.7 times higher than that of PBS control.

The apical region is the terminal of targeted tooth 100 connected to the alveolar bone (apex region of the root of tooth).

The SP cell is an undifferentiated cell discovered by Goodel et al. (J. Exp. Med. vol. 183, 1996) and it is a cell group that appears at a position on flow cytometry different from that of the normal cells (cells other than undifferentiated cell) ("Hoechst Blue-weakly positive and Hoechst Red-weakly positive"), as it emits fluorescence at 405 nm and 600 nm when excited by UV in flow cytometric analysis after a fluorescent colorant Hoechst 33342 is incorporated in therein.

The dental pulp SP cells are preferably CD31-negative/CD146-negative cells, CD24-positive cells, CD105 positive cells or CD150-positive cells.

The content of the dental pulp stem cells in the root canal filler is preferably $1\times10^3$ cell/μl or more and $1\times10^6$ cell/μl or less. It is because a dental pulp stem cell content of less than $1\times10^3$ cell/μl may lead to insufficient regeneration of the dental tissue in root canal. On the other hand, a dental pulp stem cell content of more than $1\times10^6$ cell/μl may cause unexpected adverse reactions to the targeted tooth.

Figure 1F:
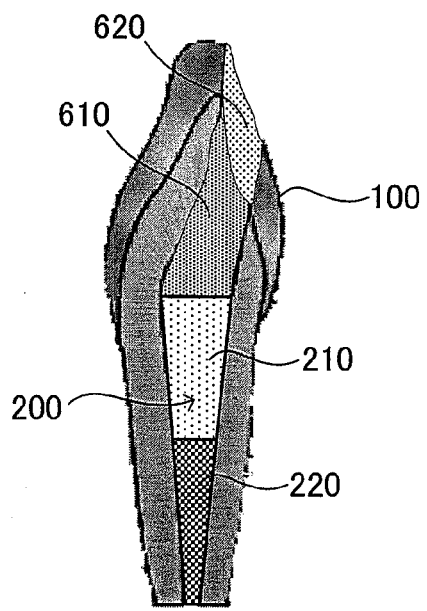
FIG. 1F is a schematic view explaining injection of Spongel (gelatin) and a resin.
Figure 1G:
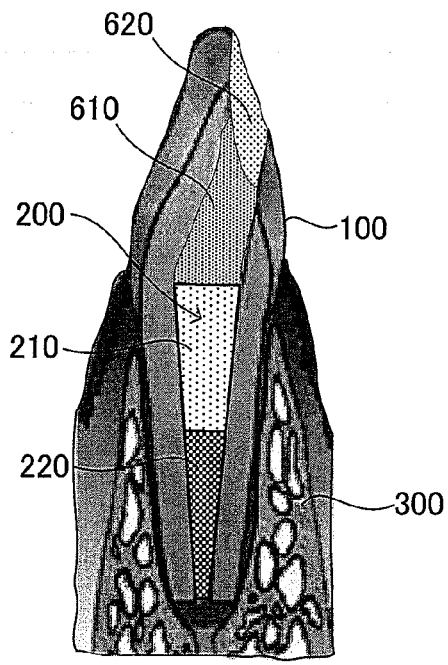
FIG. 1G is a schematic view explaining replantation in odontectomy cavity.

After injection of the root canal filler into the apical side of the root canal, as shown in FIG. 1F, gelatin 610 is injected to the region above the root canal filler 200 and the root canal is capped with a resin 620. Then as shown in FIG. 1G, the extracted tooth is replanted into the odontectomized cavity 300.

Figure 1H:
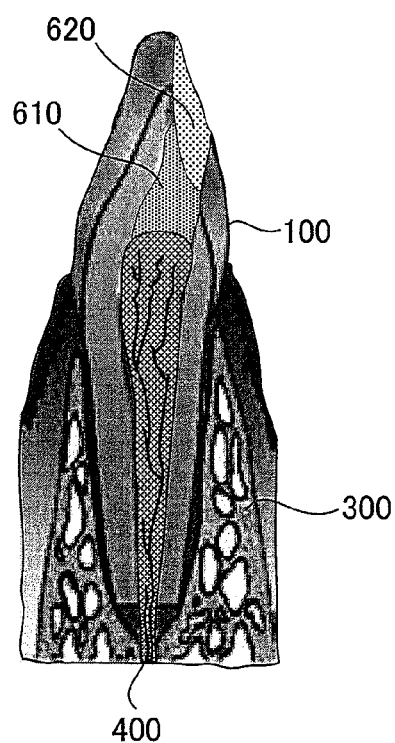
FIG. 1H is a schematic view illustrating dental pulp regeneration and vasculogenesis/angiogenesis.
Figure 1I:
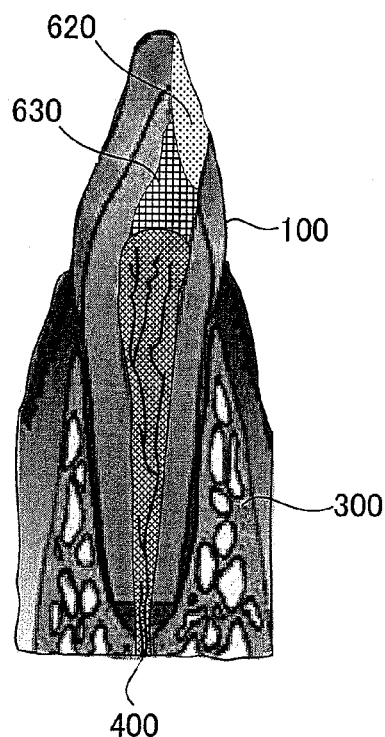
FIG. 1I is a schematic view explaining injection of a morphogen and a resin.
Figure 1J:
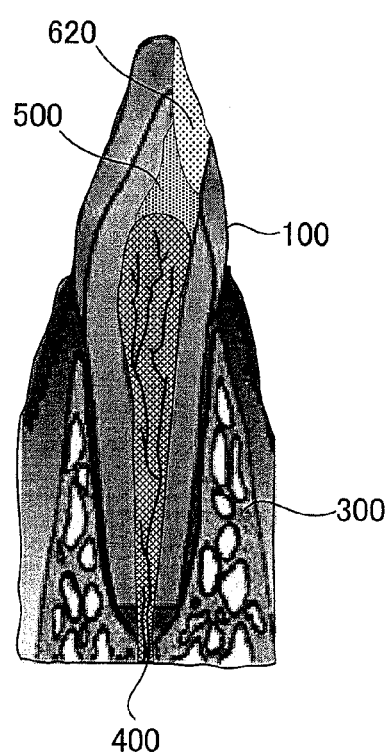
FIG. 1J is a schematic view showing dentin regeneration.

In this way, the dental tissue in the root canal is regenerated. The regenerated dental tissues are, for example, blood vessel 400 and dental pulp tissue in the root canal, as shown in FIG. 1H. Then, the resin 620 is removed once; a morphogen 630 such as BMP or a growth/differentiation factor is applied on the tooth-crown dental pulp; and the root canal is capped with the resin 620, as shown in FIG. 1I. Dentin 500 is also regenerated, when the morphogen 630 or the growth/differentiation factor is applied on the tooth-crown dental pulp, as shown in FIG. 1J. Tissues that can be regenerated are not limited thereto, and nerve regeneration is also accelerated.

Figure 1K:
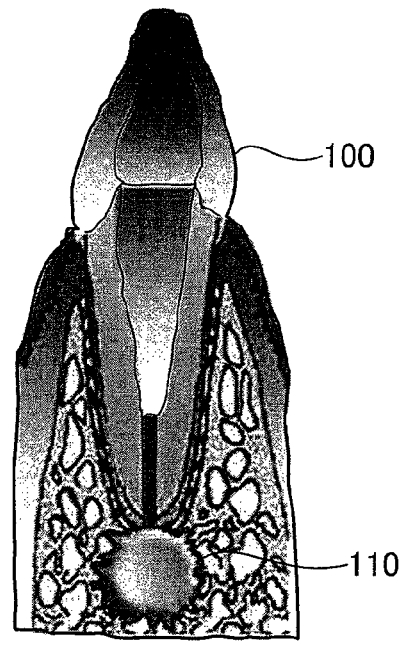
FIG. 1K is a schematic view illustrating a periapical periodontitis in which bacteria reach dentinal wall and periapical tissue.

The targeted tooth 100 is a tooth in which microbial infection reaches coronal pulp or radicular pulp because of caries, pulpitis, etc. in embodiment 1 described above, but it is not limited thereto, and the targeted teeth 100 also include a tooth of which the sense of occlusion is weakened by deterioration in nerve function. it is possible in such a case to improve the occlusion sense by regenerating the dental pulp, by injecting a root canal filler after pulpectomy. As shown in FIG. 1K, the targeted teeth 100 also include a tooth in which microbial infection reaches apical periodontal tissue (tooth in which microbes reach the dental pulp and additionally to dentin of root canal wall and apical periodontal tissue). Such a tooth often has periapical disease 110 additionally. A root canal filler 200 is injected into the root canal after enlargement and disinfectant. The infected root canal is a root canal in which microbes reach dental pulp and additionally dentin of root canal wall, and the phrase "after enlargement and disinfectant of the root canal" means after removal of the microbes in the infected root canal.

(Embodiment 2)

Figure 2A:
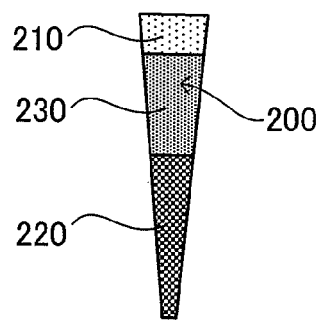
FIG. 2A is a schematic view explaining a root canal filler having cells enriched for dental pulp stem cells attached in the apical side of the root canal and a chemotactic factor attached in the tooth crown-side of the root canal.
Figure 2B:
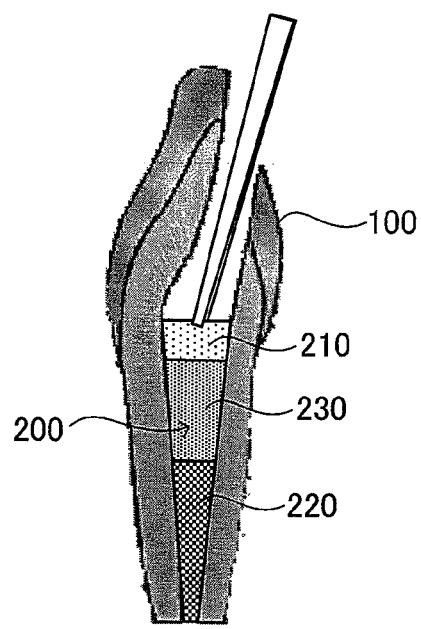
FIG. 2B is a schematic view explaining insertion of the root canal filler.

Hereinafter, the dental tissue regeneration method in embodiment 2 will be described with reference to FIGS. 2A to 2C. In a typical example of the method of producing the root canal filler 200, 30 to 40 μl of collagen mixture (mixing rate of type I and III collagens: 1:1) with a chemotactic factor is first absorbed, and 20 μl to 30 μl of collagen mixture with cells including dental pulp stem cells is then absorbed into the tip of Pipetman, to a total volume of 60 μl. Also in embodiment 2, absorption, for example into the tip of Pipetman is preferable to be sufficiently slow so that no air bubble is generated. The internal diameter of the Pipetman tip is preferably smaller. In this way, the root canal filler 200 shown in FIG. 2A is produced. As described above, in the case of the root canal filler 200, cells including dental pulp stem cells 220 are absorbed in the apical part of the root canal, and a chemotactic factor 230 containing at least one of cell chemotactic factor, cell growth factor and neurotrophic factor is absorbed in the crown part of the root canal (e.g. top ½ to ⅔ of root canal). The reasons for absorbing the cells including dental pulp stem cells 220 in the apical part of the root canal and a chemotactic factor 230 in the crown part of the root canal are that there is a possibility of no supply of nutrition from tissue and the resultant necrosis of the cells including dental pulp stem cells 220 even if the cells are absorbed in the crown part of the root canal. The cells including dental pulp stem cells absorbed in the apical part of the root canal often accelerate dental tissue regeneration easily, as the cells migrate by the chemotactic factor absorbed in the crown part of the root canal. As shown in FIG. 2A, it is possible to leave the extracellular matrix 210 in the root-canal crown side of the root canal filler 200.

As shown in FIG. 1D in embodiment 1, the targeted tooth 100 is subjected to pulpectomy and the post-pulpectomy root canal is enlarged. Then as shown in FIG. 2B, the root canal filler 200 is injected into the apical part of the root canal.

The cell chemotactic factor means a molecule that activates signal transmission system involved in cell migration, as it binds to the receptor. Alternatively, the cell growth factor means a molecule that activates signal transmission system involved in cell growth, as it binds to the receptor. Yet alternatively, the neurotrophic factor means a molecule that activates signal transmission system involved in cell survival, as it binds to the receptor.

The cell chemotactic factor for use is preferably at least one of SDF1, VEGF, GCSF, MMP3, Slit and GMCSF. In particular, MMP3, which has high cell migration potential, can be used highly favorably.

The cell growth factor for use is preferably at least one of bFGF and PDGF.

The neurotrophic factor for use is preferably at least one of GDNF, BDNF and NGF.

The content of the chemotactic factor in the extracellular matrix carrying the attached chemotactic factor is preferably 0.1 ng/μl or more and 500 ng/μl or less. It is because a chemotactic factor content of less than 0.1 ng/μl may possibly lead to decrease in migration activity. Alternatively, a chemotactic factor content of more than 500 ng/μl may cause unexpected adverse effects on the targeted tooth 100.

Similarly to embodiment 1, the extracellular matrix is preferably made of a biocompatible material containing at least one of collagen, synthetic proteoglycans, gelatin, hydrogel, fibrin, phosphophorin, heparan sulfate, heparin, laminin, fibronectin, alginic acid, hyaluronic acid, chitin, PLA, PLGA, PEG, PGA, PDLLA, PCL, hydroxyapatite, β-TCP, calcium carbonate, titanium and gold.

The collagen is preferably a collagen mixture of type I and III collagens. The rate of the type III collagen in the collagen mixture described above is preferably 30 wt % or more and 50 wt % or less.

Figure 2C:
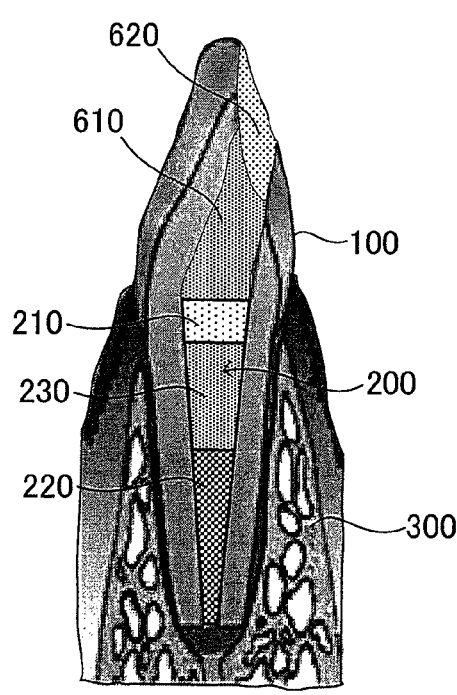
FIG. 2C is a schematic view explaining replantation in the odontectomy cavity.

Then similarly to FIG. 1F of embodiment 1, gelatin 610 is injected; the root canal is capped with a resin 620; and, as shown in FIG. 2C, the extracted tooth is replanted in the odontectomised cavity 300. Subsequently as shown in FIG. 1H, the blood vessel 400 and the dental pulp tissue in the root canal are regenerated, but the regeneration rate is higher in the present embodiment than in embodiment 1. As shown in FIG. 1I, a morphogen such as BMP 630 or a growth/differentiation factor is applied to the tooth crown-sided dental pulp, for dentin regeneration as shown in FIG. 1J, but the regeneration rate is improved in the present embodiment than in embodiment 1.

Also in embodiment 2 described above, the root canal filler 200 may be injected into the targeted tooth 100 after enlargement and cleaning of the infected root canal with periapical disease.

EXAMPLE 1

{Fractionation and Characterization of Cells}

Figure 3:
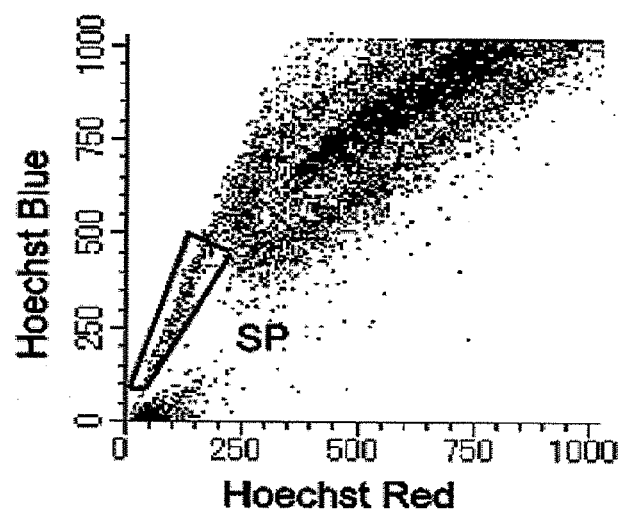
FIG. 3 is a graph explaining the flow cytometric analysis of SP cells.

Porcine tooth germ was extracted and enzyme-digested with collagenase at 37° C. for 1 hour and a half for separation of dental pulp cells; the cells were dispersed in DMEM containing 2% serum at a concentration of $1 \times 10^6$ cells/ml and labeled with 5 μg/ml Hoechst 33342. The cells were then labeled with CD31 and CD146 antibodies at 4° C. for 30 minutes, before analysis by flow cytometry. FIG. 3 shows the analytical results obtained by flow cytometry of the SP cells. The content of the porcine dental pulp-derived SP cells was 0.2% in the entire cells.

Figure 4:
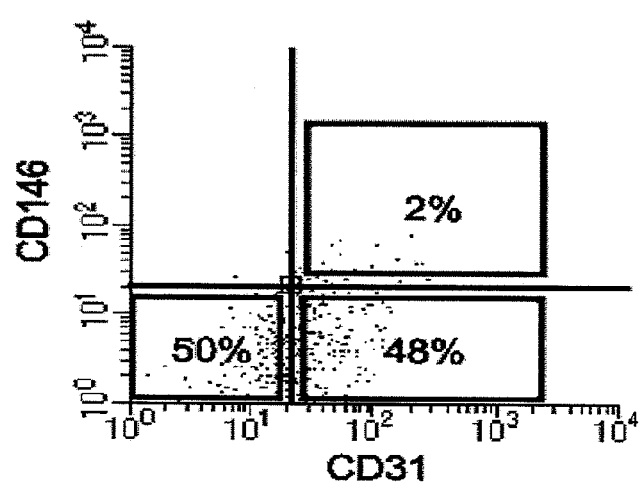
FIG. 4 is a graph showing fractionation of SP cells after labeling with CD31 and CD146 antibodies.

As shown in FIG. 4, three fractions of dental pulp-derived SP cells: CD31$^-$/CD146$^-$ fraction; CD31$^+$/CD146$^-$ fraction and CD31$^+$/CD146$^+$ fraction were obtained. Further fractionation of the SP cells after labeling with CD31 and CD146 antibodies showed CD31$^-$/CD146$^-$ SP cells, CD31$^+$/CD146$^-$ SP cells, and CD31$^+$/CD146$^+$SP cells, representing 50%, 48% and 2%, respectively. The cells were cultured in an EBM2 medium containing EGF and IGF-I and also 10% fetal calf serum.

As shown in Table 1, flow cytometric analyses showed that CD34$^+$ and VEGFR2/FLK1$^+$ cells are present in the CD31$^-$/CD146$^-$ SP cells at approximately 70 to 90%, and there was no CD11b or CD14. Real-time RT-PCR showed that no CD11b, CD14 or CD45 mRNA was expressed, indicating that the cells were different from the stem cells in hematopoietic system.

TABLE 1

| Markers | CD31$^-$; CD146$^-$SP | CD31$^+$SP |
|---|---|---|
| CD31 | 0.0% | 100.0% |
| CD146 | 0.0% | 7.0% |
| CD11b | 0.0% | 0.0% |
| CD14 | 0.0% | 0.0% |
| CD34$^+$ | 69.0% | 93.0% |
| VEGFR2/FLK1$^+$ | 87.0% | 98.0% |
| CD90 | 0.2% | 0.2% |
| CD117/c-kit | 0.0% | 0.0% |
| CD150 | 0.0% | 0.0% |
| CD271/LNGFR | 94.0% | 70.0% |

As shown in Table 2, CD133 mRNA expressed in bone marrow-derived angioblasts was not observed at all in dental pulp-derived CD31$^-$/CD146$^-$ SP cells.

TABLE 2

| | CD31$^-$SP/Pulpal tissue | CD31$^+$SP/Pulpal tissue |
|---|---|---|
| CD11b | 0.0 | 0.0 |
| CD14 | 0.0 | 0.0 |
| CD45 | 0.0 | 0.0 |
| CD133 | 0.0 | 0.0 |
| sox2 | 12.0 | 5.0 |
| Bcrp1 | 34.0 | 8.0 |
| CXCR4 | 12.0 | 1.5 |
| Stat3 | 730.0 | 560.0 |

TABLE 2-continued

| | CD31$^-$SP/Pulpal tissue | CD31$^+$SP/Pulpal tissue |
|---|---|---|
| Bmi1 | 450.0 | 300.0 |
| Tert | 30.0 | 0.8 |

Comparison of RNA expression between dental pulp-derived CD31$^-$/CD146$^-$ SP cells and dental pulp-derived CD31$^+$/CD146$^-$ SP cells, as determined by microarray and real-time RT-PCR, shows that vascular endodermal growth factor (VEGF-A), cytokines (G-CSF, GM-CSF, MCP1/CCL2, and MDCF I), extracellular matrix-decomposing enzymes (MMP1, MMP3 and Arginase I) and others (GP38K and CRSP) were expressed significantly, as shown in Table 3.

TABLE 3

| | Dental pulp CD31$^-$ SP/pulpal tissue | dental pulp CD31$^+$ SP/pulpal tissue |
|---|---|---|
| VEGF-A | 154.3 | 65.3 |
| HGF | 1.0 | 0.1 |
| G-CSF | 26.9 | 0.2 |
| GM-CSF | 1260.7 | 1.2 |
| MCP1/CCL2 | 30.3 | 0.6 |
| CXCL2 | 26.9 | 0.1 |
| MDCF I | 1243.3 | 21.6 |
| MDCF II | 2033.9 | 0.1 |
| TF | 42.2 | 0.8 |
| SDF1 | 1.2 | 23.9 |
| IL-1α | 229.1 | 2.7 |
| IL-6 | 257.8 | 4.5 |
| IL-12 | 0.8 | 4.0 |
| LIF | 128.0 | 1.7 |
| MMP1 | 3281.2 | 0.8 |
| MMP2 | 1.4 | 0.7 |
| MMP3 | 61.4 | 0.0 |
| MMP9 | 1.3 | 0.2 |
| Arginase I | 68.1 | 3.6 |
| Lipoprotein lipase | 4.5 | 0.1 |
| Dipeptidyl peptidase IV | 1.1 | 0.0 |
| SHAS2 | 30.7 | 0.3 |
| PTHLH | 0.6 | 0.0 |
| Integrin, beta-like 1 | 12.7 | 0.3 |
| GP38K | 657.1 | 0.1 |
| CRSP | 50.2 | 0.1 |

{Multilineage Differentiation Potential}

The CD31$^-$/CD146$^-$ SP cells showed an extensive networks of cords and tube-like structures 24 hours after vasculogenic induction on Matrigel. The CD31$^+$SP cells did showed a smaller number of cords. In addition, the CD31$^-$/CD146$^-$ SP cells formed a blood vessel-like structure in Matrigel 10 days after, and the cells surrounding the blood vessel-like structure expressed endothelial cell differentiation marker of CEACAM1, CD146 and occludin mRNA. Also 10 days after culture in the presence of VEGF and bFGF, the cells expressed endothelial cell differentiation marker of CD31, vWF, and VE-cadherin. In addition, the CD31$^-$/CD146$^-$ SP cells showed histamine-induced release of vWF and incorporation of ac-LDL, functional properties of endothelial cell. Further, the CD31$^-$/CD146$^-$ SP cells showed multipotency and differentiated into cartilage, fat, nerve, and odontoblasts by induction in vitro.

{Migration Potential and Proliferation Potential}

The CD31$^-$/CD146$^-$ SP cells showed higher proliferation potential by bFGF and EGF stimulus in vitro, compared to other two fractions. In addition, the CD31$^-$/CD146$^-$ SP cells showed twice higher migration potential, as induced by VEGF and SDF1, compared to other two fractions.

Figure 5A:
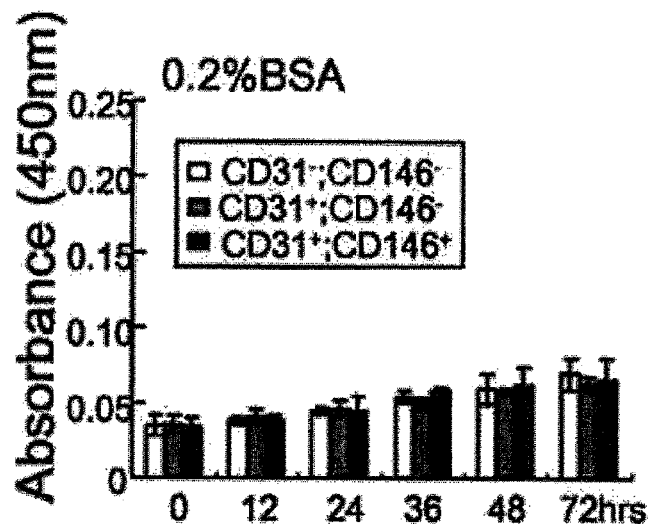
FIG. 5A is a graph explaining the proliferating activity of CD31⁻/CD146⁻ SP cells in the control of 0.2% BSA.
Figure 5B:
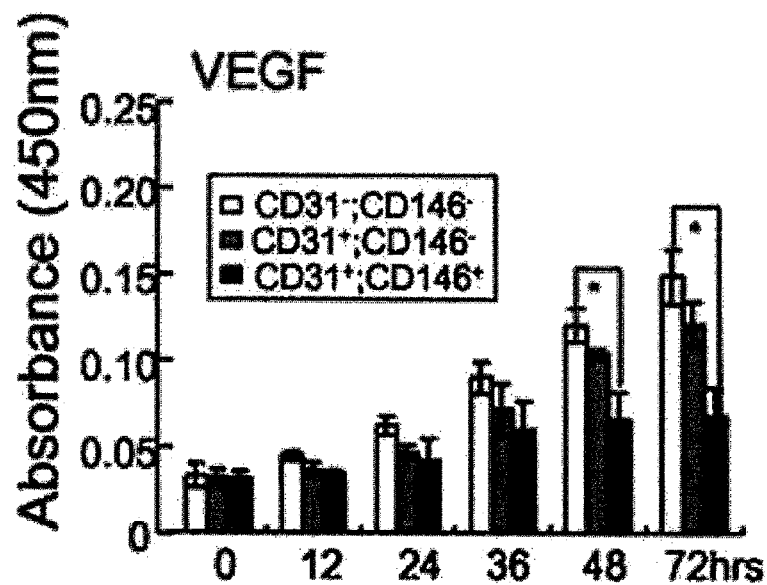
FIG. 5B is a graph explaining the proliferating activity of CD31⁻/CD146⁻ SP cells in the presence of 50 ng/ml VEGF.
Figure 5C:
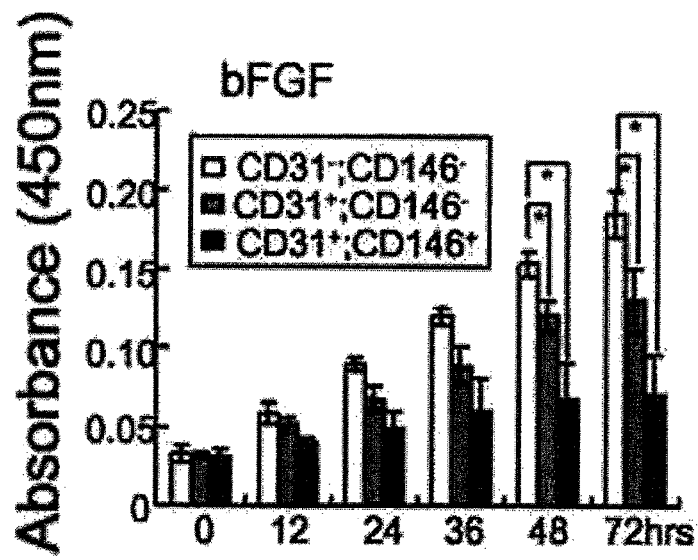
FIG. 5C is a graph explaining the proliferating activity of CD31⁻/CD146⁻ SP cells in the presence of 50 ng/ml bFGF.
Figure 5D:
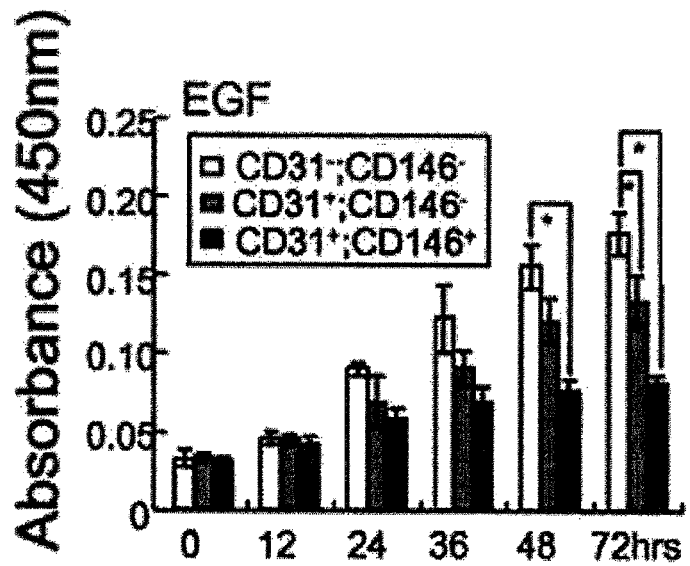
FIG. 5D is a graph explaining the proliferating activity of CD31⁻/CD146⁻ SP cells in the presence of 50 ng/ml EGF.
Figure 5E:
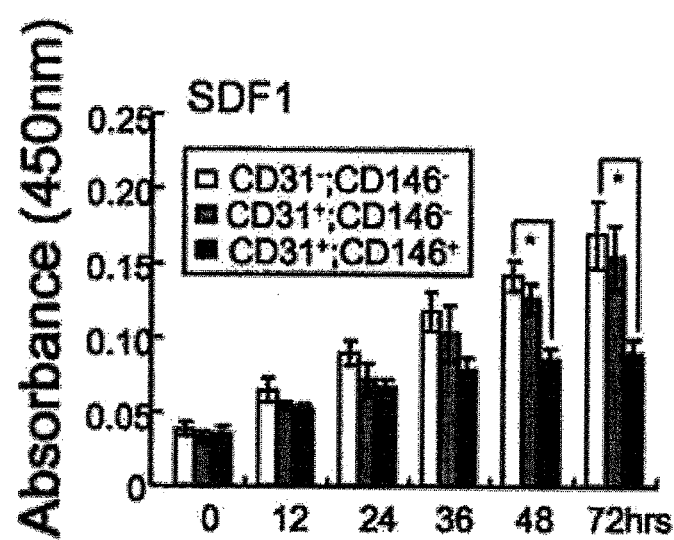
FIG. 5E is a graph explaining the proliferating activity of CD31⁻/CD146⁻ SP cells in the presence of 50 ng/ml SDF1.
Figure 5F:
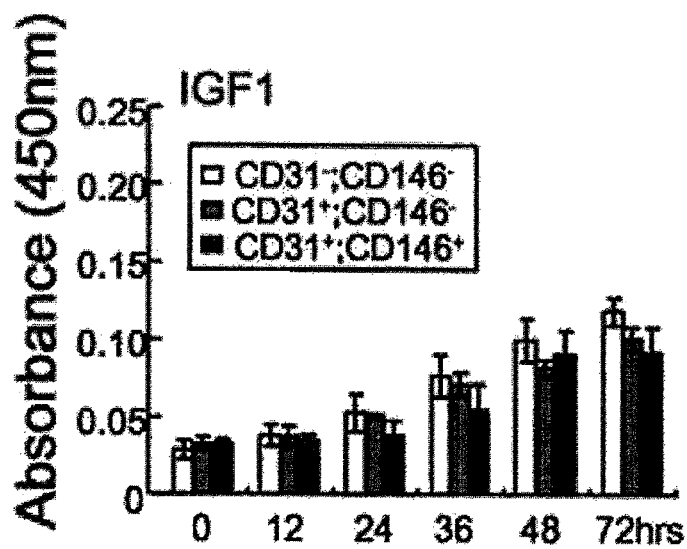
FIG. 5F is a graph explaining the proliferating activity of CD31⁻/CD146⁻ SP cells in the presence of 50 ng/ml IGF1.

FIG. 5A corresponds to a control of 0.2% BSA; FIG. 5B corresponds to 50 ng/ml VEGF; FIG. 5C corresponds to 50 ng/ml bFGF; FIG. 5D corresponds to 50 ng/ml EGF; FIG. 5E corresponds to 50 ng/ml SDF1; and FIG. 5F corresponds to 50 ng/ml IGF1. After addition of Tetra-color one (registered trade name), the cell count was monitored at 450 nm after 0, 12, 24, 36, 48, and 72 hours. The CD31$^-$/CD146$^-$ SP cells showed high proliferating activity in the presence of bFGF or EGF after 72 hours, compared to other fractions. The data is the average±SD of four samples (*P<0.01). The experiment was repeated three times, and one representative experiment was presented.

Figure 6:
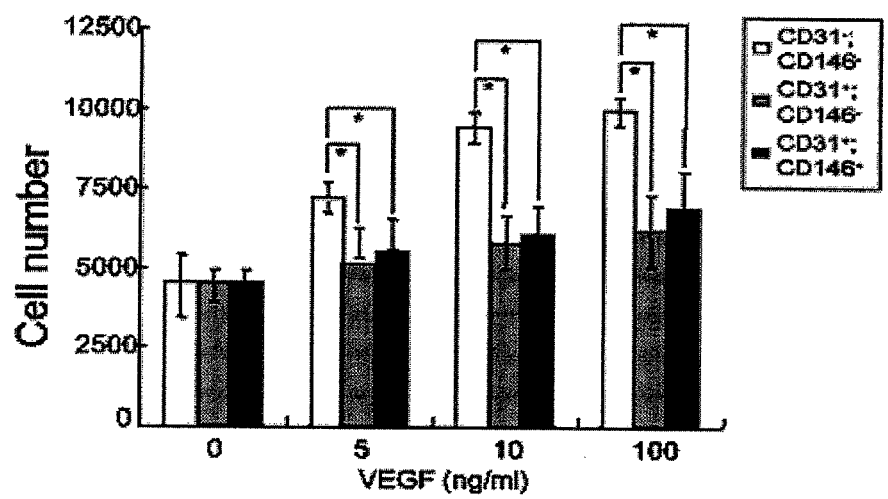
FIG. 6 is a graph showing the migration activity of CD31⁻/CD146⁻ SP cells in the various concentrations of VEGF.

As shown in FIG. 6, VEGF-A was added to 24-well medium at the final concentration of 0, 5, 10 and 100 ng/ml; $5 \times 10^4$ cells were inoculated on a PET-membrane insert; and cells passing through the membrane were counted after 24 hours. The CD31$^-$/CD146$^-$ SP cells have high migration potential, showing concentration-dependent. The data is the average±SD of four samples (*P<0.01). The experiment was repeated three times and one representative experiment was presented.

Figure 7:
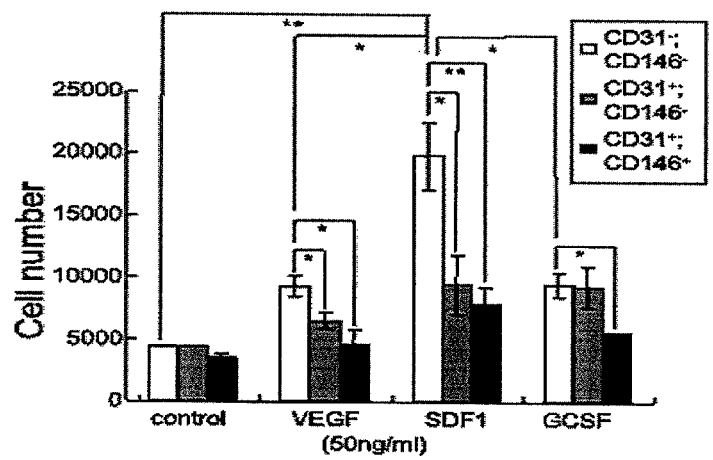
FIG. 7 is a graph showing the migration activity of CD31⁻/CD146⁻ SP cells with the various chemotactic factors.

As shown in FIG. 7, the change in migration potential by addition of VEGF-A, SDF1 and GCSF was determined. The results indicated that SDF1 and VEGF-A accelerate migration of the CD31$^-$/CD146$^-$ SP cells. The data is the average±SD of four samples (*P<0.01, **P<0.001). The experiment was repeated three times and one representative experiment was presented.

Thus when the conditioned medium of the CD31$^-$/CD146$^-$ SP cells were applied in vitro to vascular endothelial cells (HUVEC) for 48 hours, the vascular endothelial cells showed a proliferating activity similar to that when they are treated with MMP3 or VEGF at a concentration of 50 ng/ml.

In addition, the conditioned medium of the CD31$^-$/CD146$^-$ SP cells showed anti-apoptotic activity to vascular endothelial cells in the magnitude similar to that of MMP3 or GM-CSF.

Figure 8:
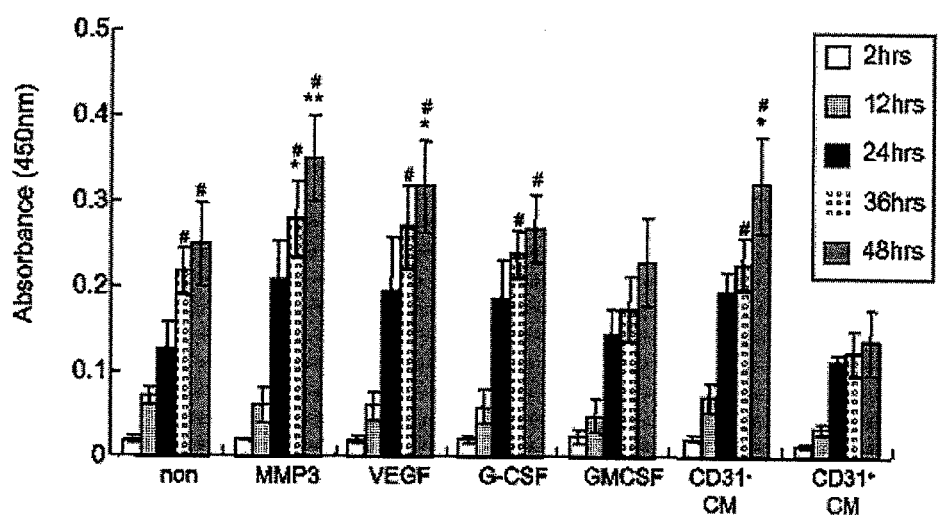
FIG. 8 is a graph showing the proliferating activity of the culture conditioned medium of dental pulp CD31⁻ and CD146⁻ SP cells to HUVEC (vascular endothelial cells).

FIG. 8 is a graph showing the HUVEC-mitogenic activity of the conditioned medium of the dental pulp CD31$^-$/CD146$^-$ SP cells. The proliferating activities of MMP3, VEGF-A, G-CSF, GM-CSF and CD31$^+$/CD146$^-$ SP conditioned medium are compared after 2, 12, 24, 36, and 48 hours. The conditioned medium of the CD31$^-$/CD146$^-$ SP cells had mitogenic activity similar to that of other cytokines after 36 and 48 hours, and statistical analyses showed that its activity was significantly higher than the conditioned medium of the CD31$^+$/CD146$^-$ SP cells (#P<0.01)**P<0.01, *P<0.05 vs control.

Figure 9:
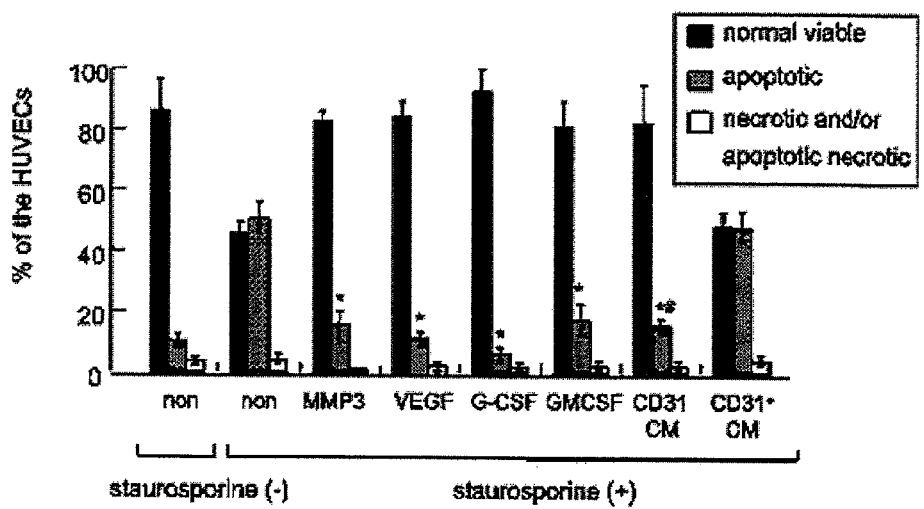
FIG. 9 is graph showing the method of measuring the ratio of necrotic cells to apoptotic cells, as determined by flowcytometry by using HUVEC (vascular endothelial cells) previously subjected to apoptosis with 100 nM staurosporine.

FIG. 9 is a graph showing the results of measurement of the ratio of necrotic cell to apoptotic cell by flow cytometry, by using HUVEC cells to which apoptosis was induced with 100 nM staurosporine. The results show that the conditioned medium of the dental pulp CD31$^-$/CD146$^-$ SP cells has high anti-apoptotic effect, similarly to MMP3, VEGF-A, G-CSF and GM-CSF, and that it has an anti-apoptotic effect statistically significantly higher than the conditioned medium of CD31$^+$/CD146$^-$ SP cells (#P<0.01). These results show that the CD31$^-$/CD146$^-$ SP cells are suitable for accelerating vasculogenesis.

{Vascularization in Mouse Hind Limb Ischemic Model}

A hindlimb ischemic model of SCID (severe combined immunodeficiency) mouse was prepared and the CD31$^-$/CD146$^-$ SP cells were transplanted in the hindlimb ischemic site. Blood flow recovered in 1 week, and neovascularization was accelerated 13 times more, compared to the CD31$^+$/CD146$^-$ SP cell transplantation group.

{Vascularization, Nerve Regeneration and Dental Pulp Regeneration in Canine Vital Tooth Pulp-Removed Model}

Figure 10:
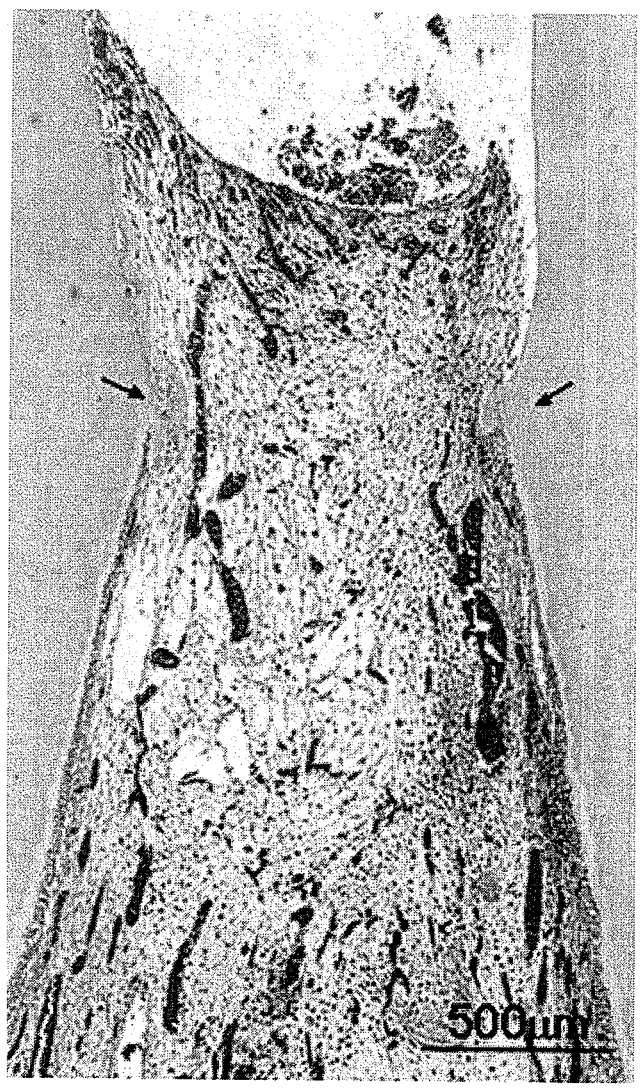
FIG. 10 is a photograph showing pulp regeneration on canine amputated pulp 14 days after transplantation of autologous dental pulp CD31$^-$/CD146$^-$ SP cells.
Figure 13:
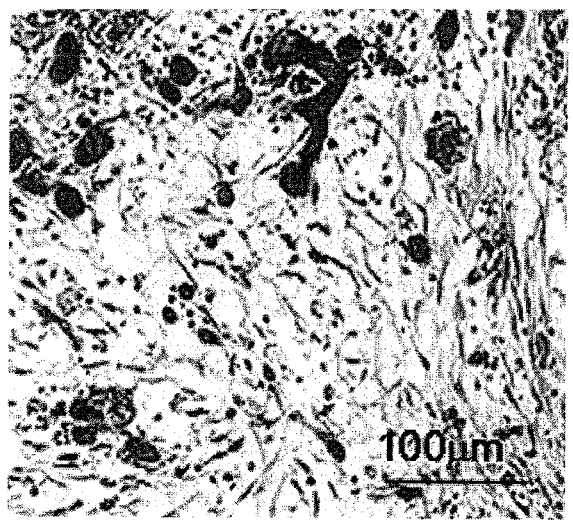
FIG. 13 is a magnified photograph of CD31$^-$/CD146$^-$ SP cells, 14 days after transplantation.

CD31$^-$/CD146$^-$ SP cells were fractionated from canine dental pulp tissue, similarly to the porcine tissue, and SP cells contained the CD31$^-$/CD146$^-$ SP cells approximately 10%. The dental pulp-derived CD31$^-$/CD146$^-$ SP cells were three-dimensionally cultured at $1 \times 10^6$ cells together with type I and III collagens. The cells were autologously transplanted on the canine amputated pulp 24 hours after culture, and the upper region of the tooth was filled with Spongel and phosphate cement and sealed additionally with a chemical-polymerization resin. CD31$^+$SP cells or type I and III collagen only were used as controls. Dental pulp was regenerated in the cavity on the amputated pulp after 14 days in the CD31$^-$/CD146$^-$ SP cell transplantation group, and new blood vessels were continuously formed in the regenerated dental pulp, extending from the remaining pulp, as shown in FIGS. 10 and 13. FIGS. 10 and 13 are photographs 14 days after autologous transplantation, each showing a tooth, to which CD31$^-$/CD146$^-$ SP cells were transplanted, —one day after three-dimensionally culture in type I and III collagens. H-E staining was used for staining. The arrows in the figure show the amputated site of the dental pulp. As shown in FIGS. 10 and 13, the cavity on the amputated pulp is filled with regenerated dental pulp tissue, and blood capillaries extending closely to the area where phosphate cement was filled.

Figure 15:
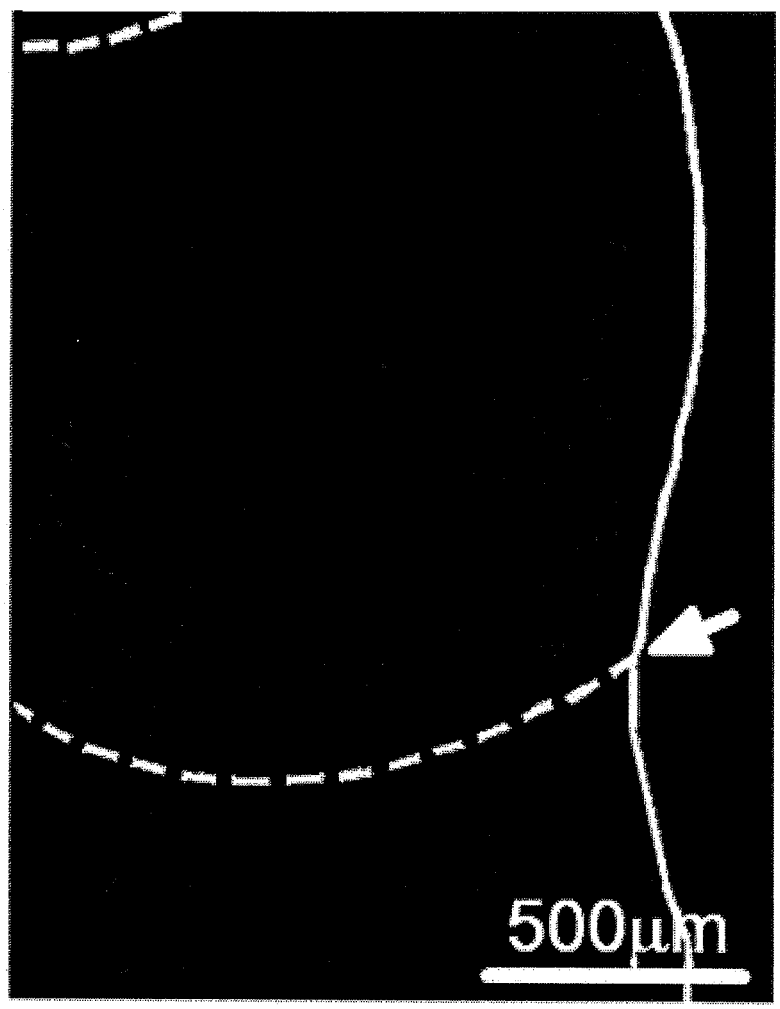
FIG. 15 is a photograph explaining CD31$^-$/CD146$^-$ SP cells observed at the bottom of the regenerated dental pulp.
Figure 17:
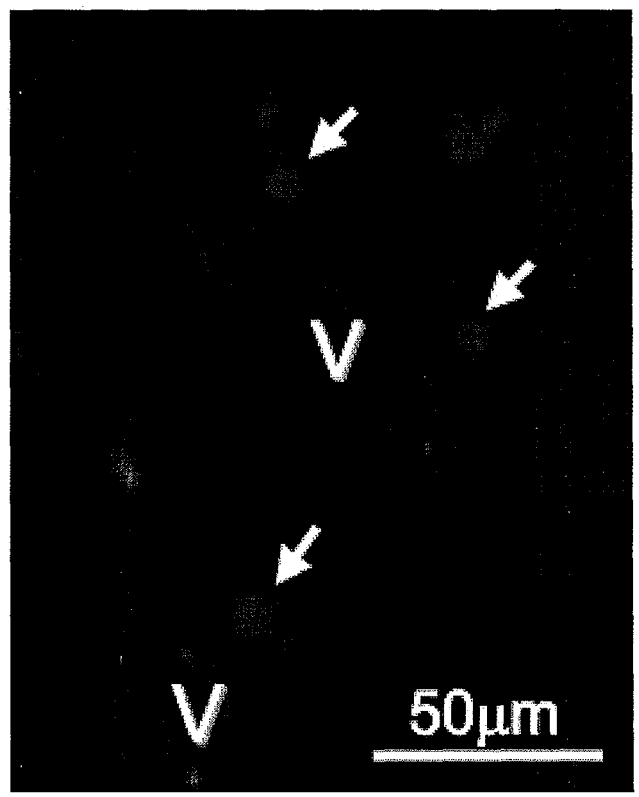
FIG. 17 is a photograph of vascular endothelial cells stained with CD146 antibody, explaining that DiI-labeled CD31$^-$/CD146$^-$ SP cells are present in the vicinity of the newly generated blood vessel.

As shown in FIGS. 15 and 17, the transplanted cells migrated to and localized in the vicinity of the newly generated blood vessel. FIG. 15 shows that the CD31$^-$/CD146$^-$ SP cells were present in the bottom region of the regenerated dental pulp. In addition, FIG. 17 is a photograph showing the vascular endothelial cells stained with CD146, demonstrating that the DiI-labeled CD31$^-$/CD146$^-$ SP cells were present in the area surrounding the newly generated blood vessel in the regenerated dental pulp tissue. The arrows in FIG. 17 show the positions of the CD31$^-$/CD146$^-$ SP cells, and the character v indicates newly generated blood vessel. The dotted lines in the figures show the boundary of the newly regenerated tissue.

Figure 11:
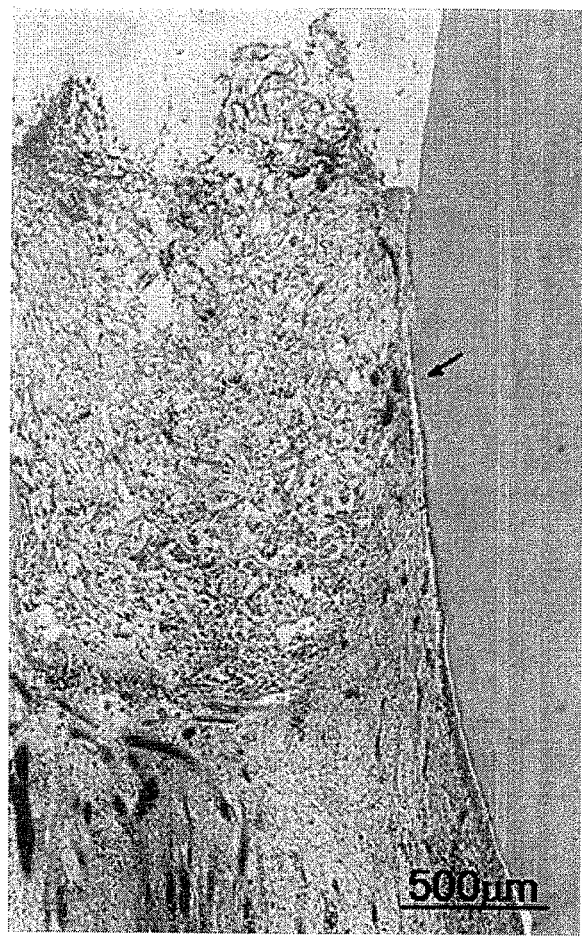
FIG. 11 is a photograph showing regeneration on canine amputated pulp 14 days after transplantation of autologous dental pulp CD31$^+$ and CD146$^-$ SP cells, 14 days after transplantation.
Figure 14:
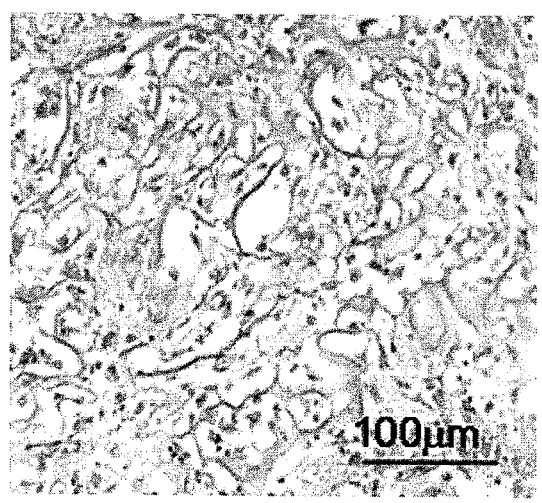
FIG. 14 is a magnified photograph of CD31$^+$/CD146$^-$ SP cells, 14 days after transplantation.
Figure 16:
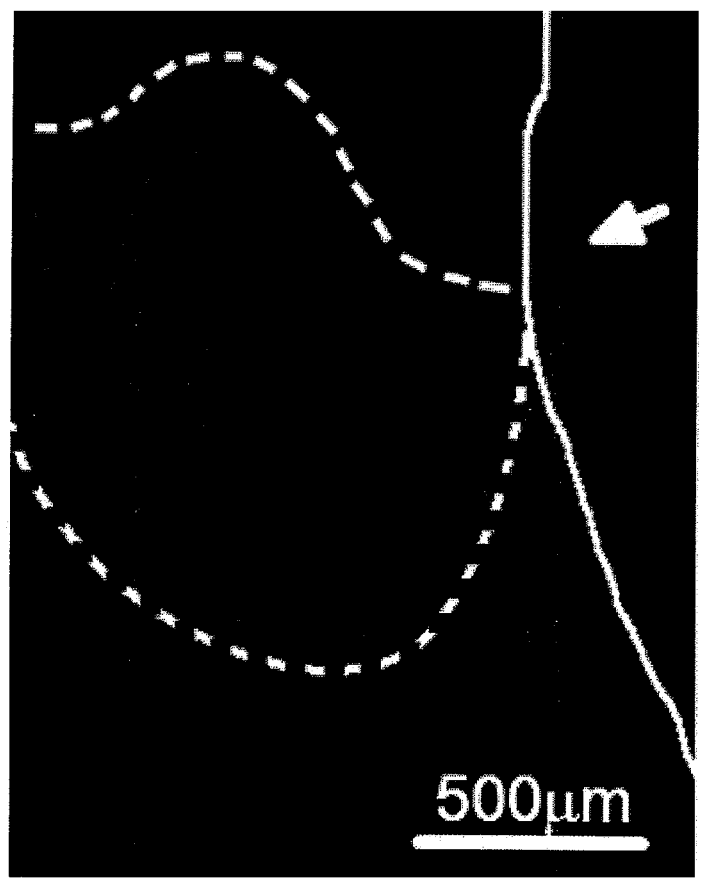
FIG. 16 is a photograph explaining CD31$^+$/CD146$^-$ SP cells present as dispersed in the entire cavity.

On the other hand, FIGS. 11, 14 and 16 are photographs of the tooth to which CD31$^+$/CD146$^-$ SP cells were transplanted. As shown in FIGS. 11, 14 and 16, transplanted cells were fixed, but there was no neovascularization or no cell migration observed in the CD31$^+$/CD146$^-$ SP cell transplantation group. FIGS. 11 and 14 show that there is a transplanted tissue fixed in the cavity but there is almost no blood capillary. FIG. 16 shows that the CD31$^+$ and CD146$^-$ SP cells are present, as dispersed in the entire cavity. The arrows indicate amputated site of the dental pulp. The white line indicates dentin wall. The dotted lines indicate the boundary of newly generated tissue.

Figure 12:
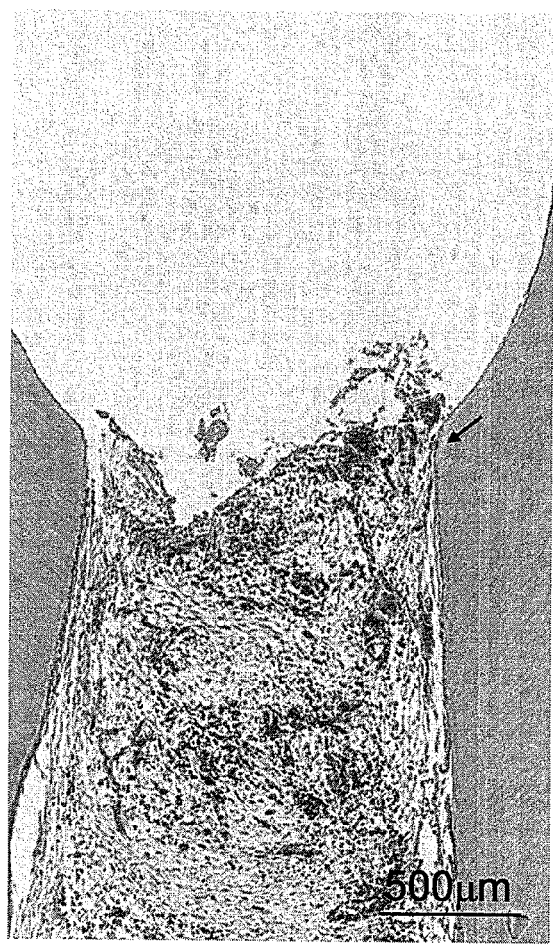
FIG. 12 is a photograph showing no regeneration on canine amputated pulp 14 days after transplantation of a cell-free collagen of type I and type III mixture.

FIG. 12 is a photograph showing a sample to which type I and III collagen only were transplanted. As shown in FIG. 12, no tissue was formed on the amputated pulp.

Figure 18:
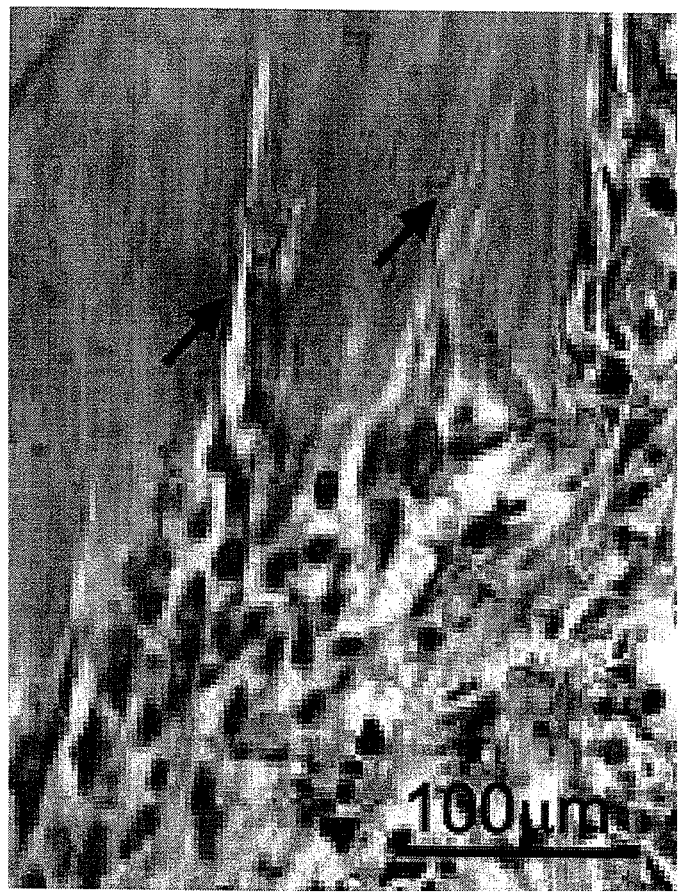
FIG. 18 is a photograph explaining that odontoblast differentiation and tubular dentin formation observed in the region in contact with phosphate cement in the upper tooth crown region.

As shown in FIG. 18, differentiation into odontoblasts and formation of tubular dentin were observed in the cavity under phosphate cement filling in the upper part of tooth crown after 28 days. The arrows in FIG. 18 indicate extensions of odontoblastic processes.

Figure 19:
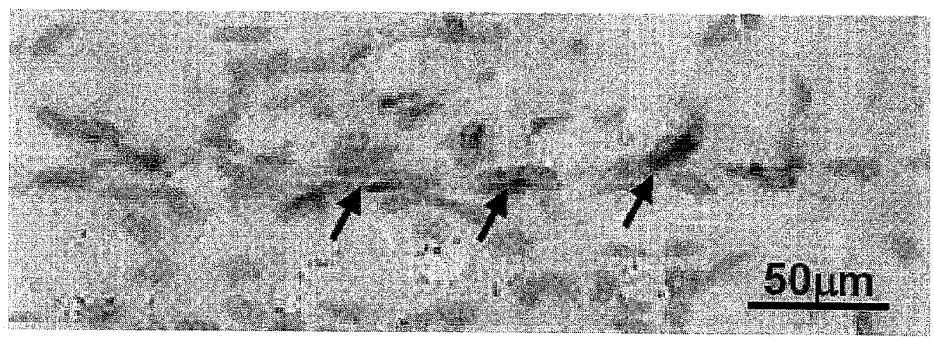
FIG. 19 is a photograph after staining with neurofilament antibody, showing that there are, in the regenerated dental pulp, neuronal processes extending from the nerves in the tooth-root dental pulp that was previously amputated.
Figure 20:
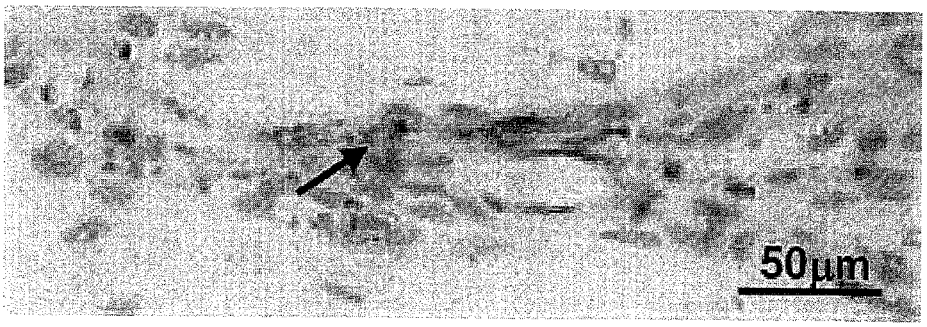
FIG. 20 is a photograph showing the neuronal process, stained by neurofilament in the original pulp tissue under the amputated site.

As shown in FIG. 19, neuronal processes were observed extending from the nerves in the amputated dental pulp in tooth root. FIG. 20 shows the cut and regenerated nerves present in remaining dental pulp of root of tooth. FIGS. 19 and 20 are photographs after neurofilament immunostaining.

EXAMPLE 2

In Example 2, regeneration of canine dental pulp after pulpectomy by using CD31$^-$/CD146$^-$ SP cells and a cell chemotactic factor SDF1 will be described.

The CD31⁻ and CD146⁻ SP cells were isolated from a canine dental pulp tissue, similarly to the porcine tissue. In addition, CD105⁺ cells were also isolated. A canine upper-jaw anterior tooth was removed; the dental pulp was removed; and the tooth was enlarged to #80 in the culture medium, to enlarge the width of the root canal in the apical area 0.8 mm or more. CD31⁻/CD146⁻ SP cells at 1×10⁶ cells were mixed with 10 μl of type I and III collagens, and injected into the apical part of ⅓ root canal within 30 minutes after extraction of tooth. In addition, 20 μl of type I and III collagens with SDF1 (200 ng) was filled into the crown part of ⅔ root canal. The tooth was replanted in the canine odontectomised cavity 300 within 30 minutes and the top of the tooth was sealed with phosphate cement and a chemical-polymerization resin. The tooth was extracted for preparation of a paraffin sample after 14 days.

Figure 21:
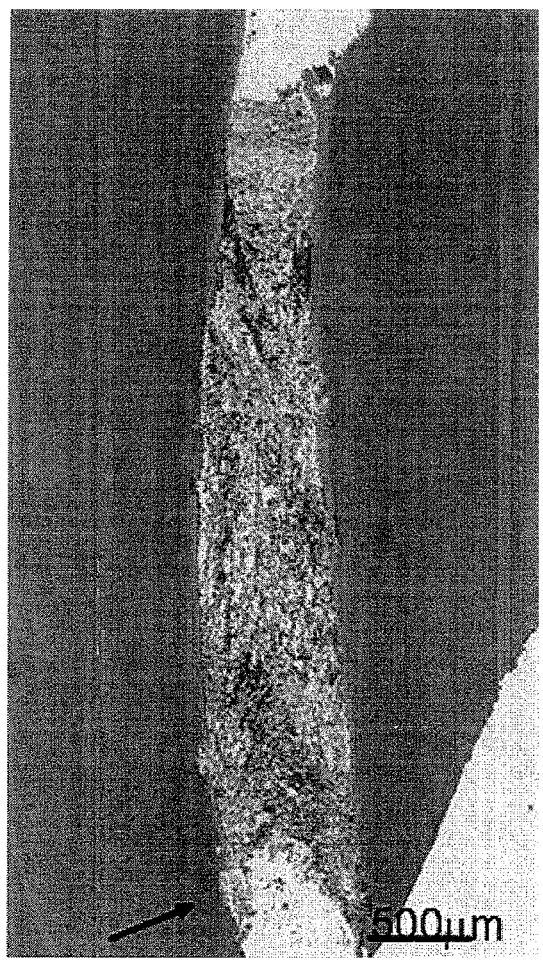
FIG. 21 is a photograph showing that almost all of the root canal is filled with regenerated dental pulp tissue 14 days after transplantation of the autologous CD31$^-$/CD146$^-$ SP cells and SDF1 absorbed in the type I and III collagen mixture into the pulpectomized root canal.
Figure 25:
FIG. 25 is a high-magnification photograph showing the newly formed capillaries in the apical part of the root canal 14 days after transplantation of SDF1 and CD31$^-$/CD146$^-$ SP cells absorbed in the type I and III collagen mixture.
Figure 26:
FIG. 26 is a high-magnification photograph showing the newly formed capillaries in the crown part of the root canal 14 days after injection of SDF1 and CD31$^-$/CD146$^-$ SP cells absorbed in the type I and III collagen mixture.
Figure 27:
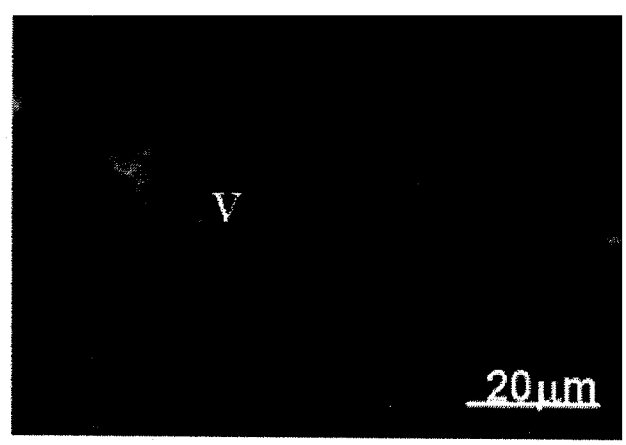
FIG. 27 is a photograph showing vascular endothelial cells stained with BS-1 lectin.
Figure 28:
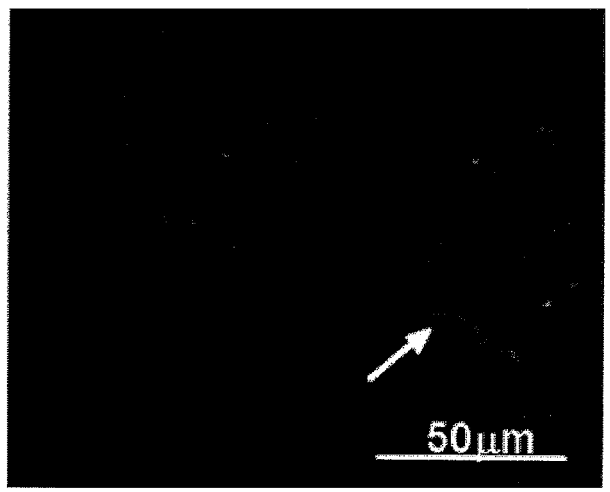
FIG. 28 is a photograph showing neuronal process after neurofilament immuno staining.

FIGS. 21, 25, 26, 27 and 28 shows the case when SDF1 (200 ng) and CD31⁻/CD146⁻ SP cells were injected to type I and III collagens. When both CD31⁻/CD146⁻ SP cells and SDF1 were used as the root canal filler, the root canal was filled with newly regenerated dental pulp tissue completely after 14 days, as shown in FIG. 21. FIG. 21 is a photograph after H-E staining. The newly regenerated dental pulp tissue had newly formed blood capillaries both in the apical side, as shown in FIG. 25, and in the tooth crown side, as shown in FIG. 26, and there was also regenerated nerves inside, as shown in FIG. 28. The character v in FIGS. 25 and 26 indicates blood capillary. FIG. 27 is a photograph showing the vascular endothelial cell stained with BS-1 lectin. FIG. 28 is a photograph after neurofilament immunostaining.

Figure 22:
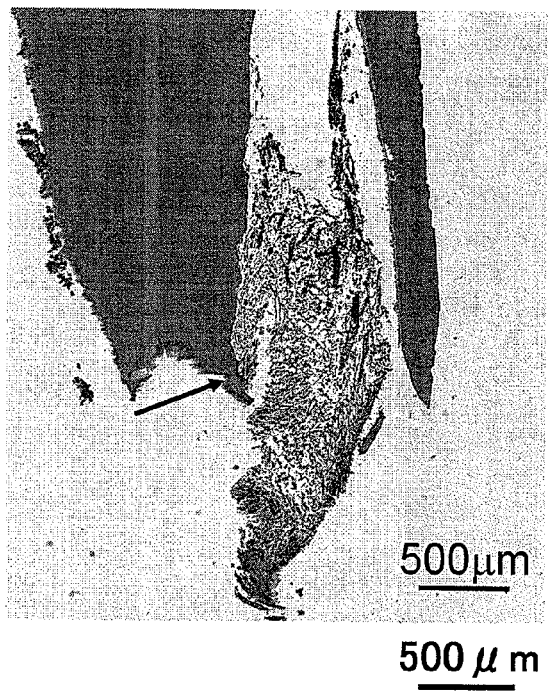
FIG. 22 is a photograph showing that only small part of the root canal is filled with regenerated dental pulp tissue 14 days after transplantation of SDF1 absorbed in the type I and III collagen mixture into the pulpectomized root canal.
Figure 23:
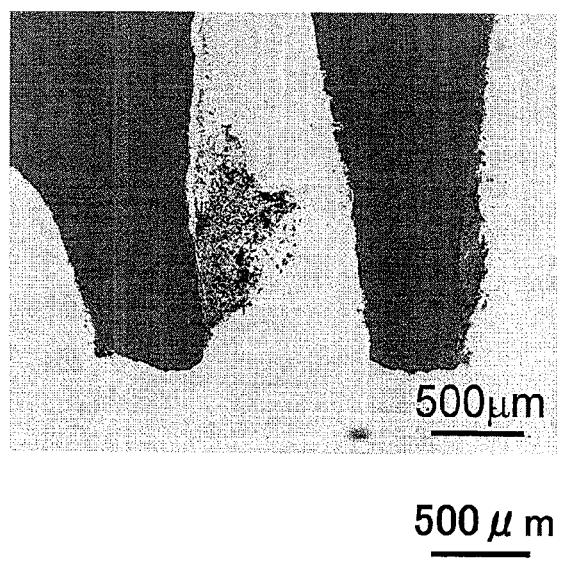
FIG. 23 is a photograph showing that only an extremely small amount of dental pulp tissue is regenerated 14 days after transplantation of only CD31$^-$/CD146$^-$ SP cells absorbed in the type I and III collagen mixture into the pulpectomized root canal.
Figure 24:
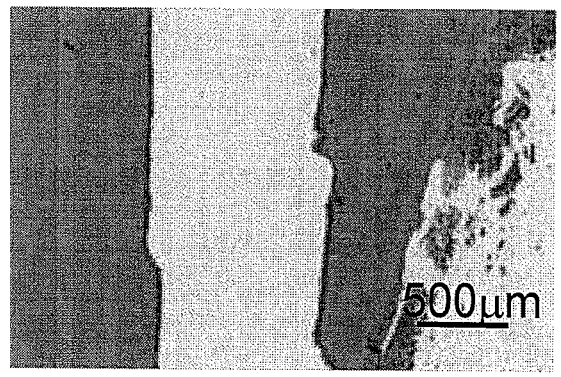
FIG. 24 is a photograph showing that no dental pulp tissue is regenerated 14 days after transplantation of the type I and III collagen mixture alone into the pulpectomized root canal.

On the other hand, when only SDF1 or CD31⁻/CD146⁻ SP cells were used, there was newly regenerated dental pulp tissue only in the apical-area ⅕ to ¼ root canal. FIG. 22 is a photograph showing the case when SDF1 (200 ng) with type I and III collagens was injected. FIG. 23 is a photography showing the case when only CD31⁻/CD146⁻ SP cells with type I and III collagens were injected. As shown in FIG. 24, almost no newly regenerated pulp tissue was observed only with type I and III collagens.

Figure 29:
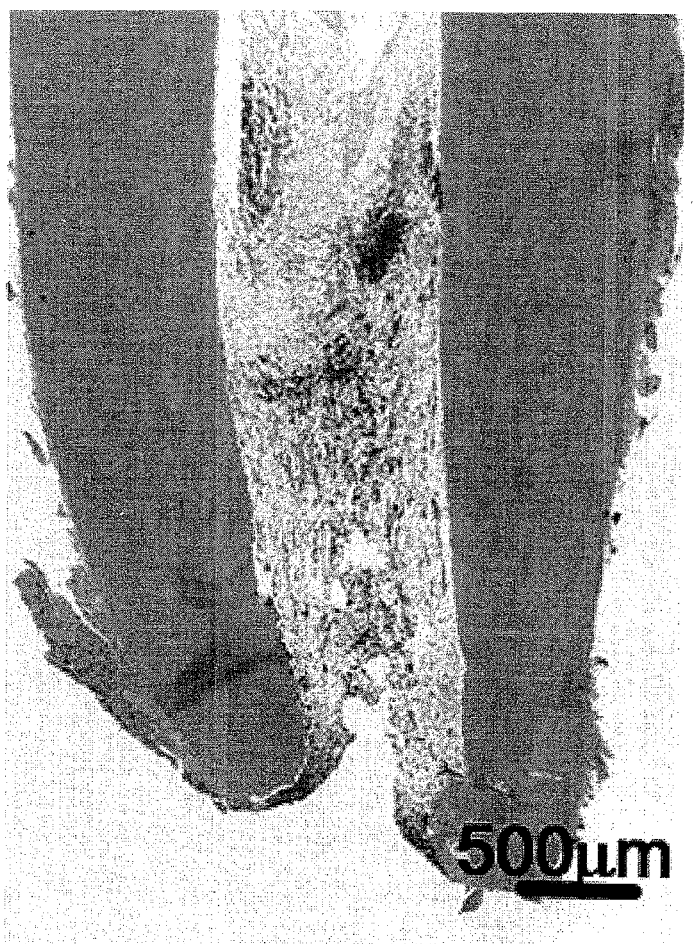
FIG. 29 is a photograph showing almost all of the root canal is filled with regenerated dental pulp tissue 14 days after transplantation of the autologous CD105$^+$ cells and SDF1 absorbed in the type I and III collagen mixture into the pulpectomized root canal.

When both CD105⁺ cells and SDF1 were used as the root canal filler, the root canal was filled with newly regenerated dental pulp tissue after 14 days, as shown in FIG. 29.

EXAMPLE 3

Mainly in Example 3, vascularization by using human permanent-tooth dental pulp CD31-negative CD146-negative SP cells and human permanent-tooth dental pulp CD105-positive cells will be described.

Figure 30:
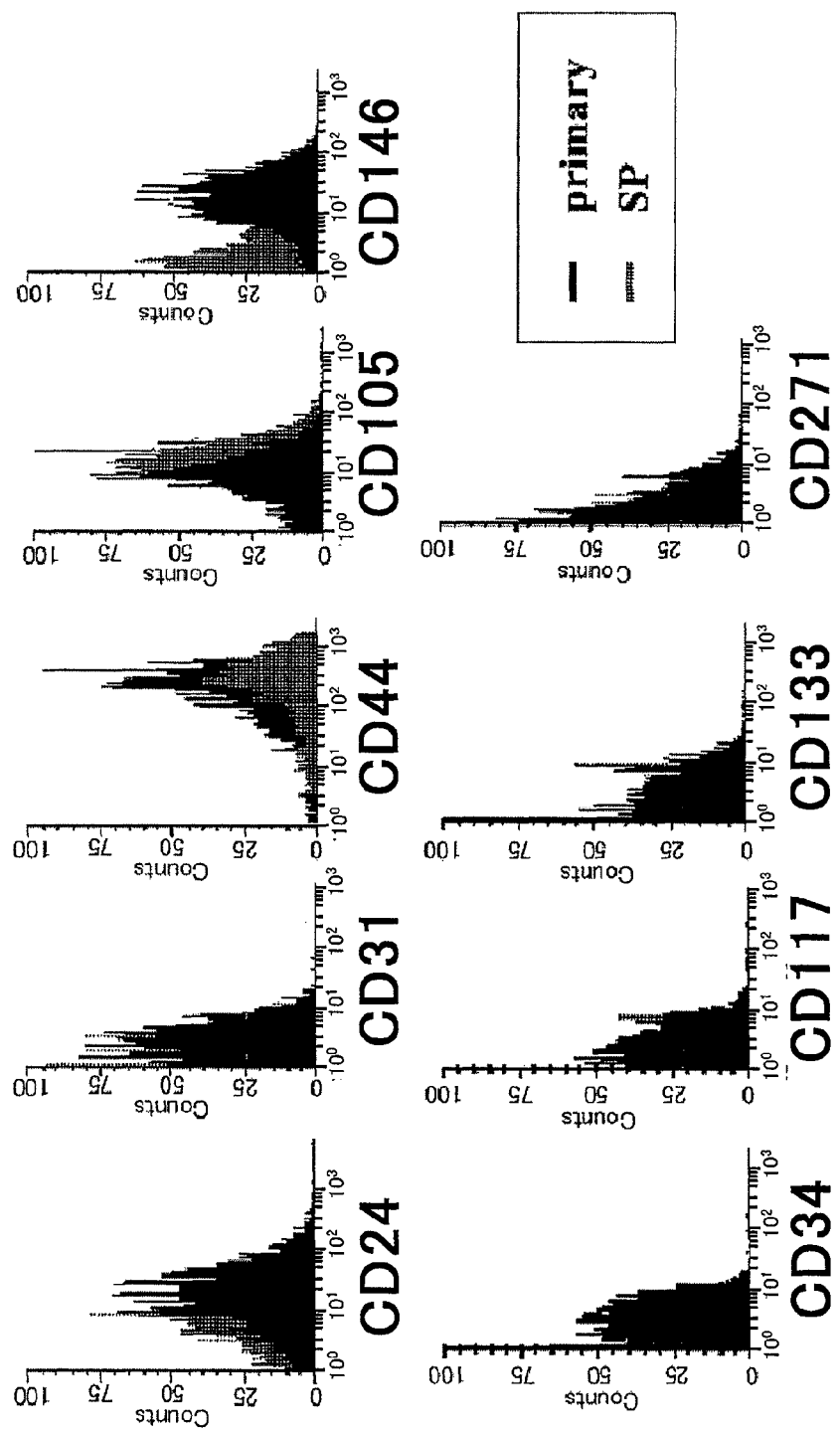
FIG. 30 is a graph showing flow cytometry of human dental pulp CD31$^-$/CD146$^-$ SP cells at the third passage of culture.

After removal of human dental pulp, the tooth was enzyme-digested with collagenase at 37° C. for 1 hour, for isolation of dental pulp cells; the cells were dispersed in DMEM containing 2% serum at a concentration of 1×10⁶ cells/ml; the cells were labeled with 5 μg/ml of Hoechst 33342 and subjected to flow cytometry using CD31 antibody, for fractionation of dental pulp CD31⁻/CD146⁻ SP cells. Separately, after isolation of dental pulp cells, they are subjected to flow cytometry using CD105 antibody, for fractionation of dental pulp CD105⁺ cells. When these cells were cultured in an EBM2 medium containing added EGF and IGF-I and also 10% fetal calf serum, the cells attached and proliferated on the dish at a frequency similar to that of the porcine dental pulp-derived cells (approximately 10%). The CD31⁻/CD146⁻ SP cells at the third passage of culture and the dental pulp CD105⁺ cells were further subjected to flow cytometry using a cell surface marker for characterization of the cells, showing that these cells were both almost positive to stem cell marker CD44, but the former cells were almost positive and the latter 30% positive to CD90. FIG. 30 shows the results of flow cytometry of the human CD31⁻/CD146⁻ SP cells. Table 4 is a table comparing human dental pulp CD31⁻/CD146⁻ SP cell, with human dental pulp CD105⁺ cell, human total pulp cell, human total deciduous tooth cell and porcine dental pulp CD31⁻/CD146⁻ SP cell. The human CD31⁻ SP cell was negative and human CD105⁺ cell almost negative to the marker CD146 of vascular endothelial cells or blood vessel smooth muscle cells. The cells were negative to CD133, which is known to be positive to bone marrow-derived angioblasts and vascular endothelial precursor cells in peripheral blood, similarly to the porcine dental pulp-derived CD31⁻/CD146⁻ SP cells, but were negative to CD34, differently from the porcine-derived cells.

When the human dental pulp CD31⁻/CD146⁻ SP cells are inoculated on Matrigel at 1×10⁴ cells/96-well and subjected to angiogenic induction in vitro, they formed an extensive

TABLE 4

Figure 31:
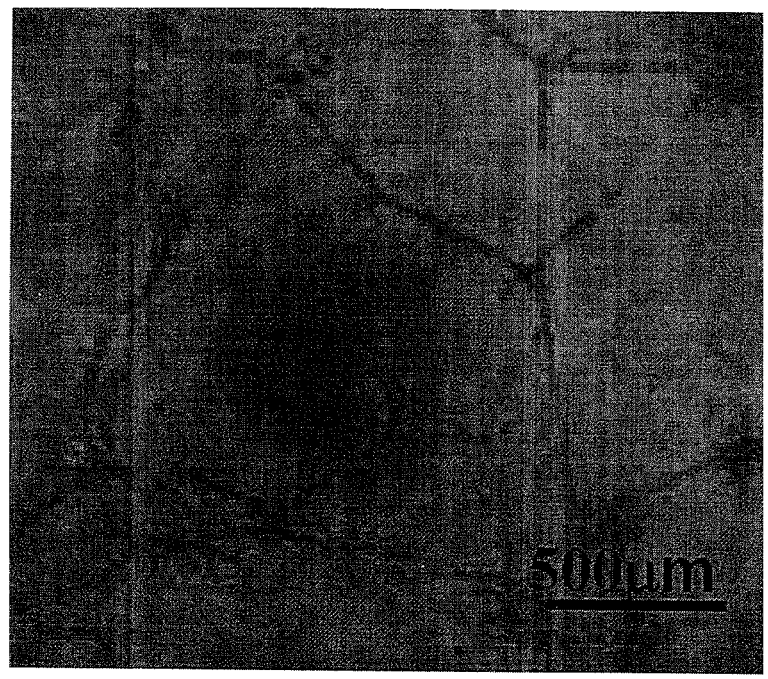
FIG. 31 is a photograph showing angiogenic potential of human dental pulp CD31$^-$/CD146$^-$ SP cells at the third passage of culture.

|  | Human CD31⁻ SP dental pulp cell | Human CD105⁺ SP dental pulp cell | Human total dental pulp cell | Human total deciduous cell | Porcine CD31⁻ SP cell |
|---|---|---|---|---|---|
| CD31 | 0.0% | 0.2% | 0.06% | 0.0% | 0.00% |
| CD146 | 0.0% | 3.0% | 40.58% | 30.6% | 0.00% |
| CD24 | 0.1% | 11.5% | 23.87% | 41.3% | — |
| CD34 | 0.01% | 0.0% | 0.01% | 0.0% | 69.0% |
| CD40 | 0.0% | 0.0% | 0.0% | 0.0% | — |
| CD44 | 92.5% | 98.9% | 91.6% | 99.9% | — |
| CD90 | 98.7% | 30.6% | 72.7% | 84.3% | 0.2% |
| CD 105 | 21.23% | 92.0% | 4.4% | 48.9% | — |
| CD117 | 0.02% | 0.0% | 0.06% | 0.05% | 0.00% |
| CD133 | 0.01% | 0.0% | 0.5% | 0.0% | 0.00% |
| CD150 | 0.21% | 3.5% | 0.1% | 0.2% | 0.00% |
| CD271 | 0.03% | 2.9% | 0.01% | 4.7% | 94.00% |
| SSEA1 | 0.29% | 0.26% | 0.06% | 0.5% | — |
| MHC class I | 18.4% | 53.0% | 66.4% | 49.0% | — |
| MHC class II | 4.6% | 3.8% | 2.0% | 5.7% | — |
| HLA-G | 2.2% | 1.1% | 1.7% | 0.3% | — | networks of cords and tube-like structures 20 hours after inoculation, as shown in FIG. 31.

Figure 32:
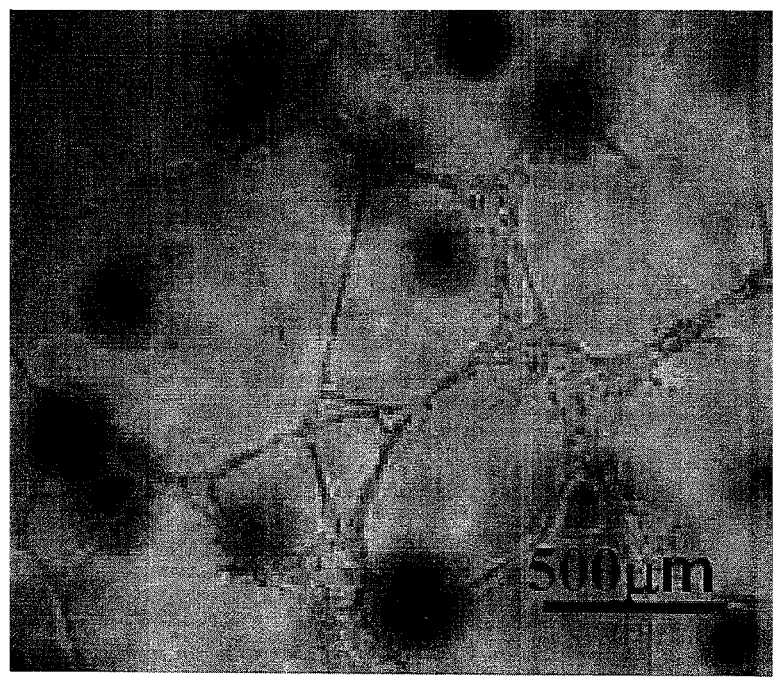
FIG. 32 is a photograph showing angiogenic potential of human dental pulp CD105$^+$ cells at the third passage of culture.

A similar experiment with human dental pulp CD105+ cell showed that the human dental pulp CD105+ cells formed an extensive networks of cords and tube-like structures, as shown in FIG. 32.

Figure 33:
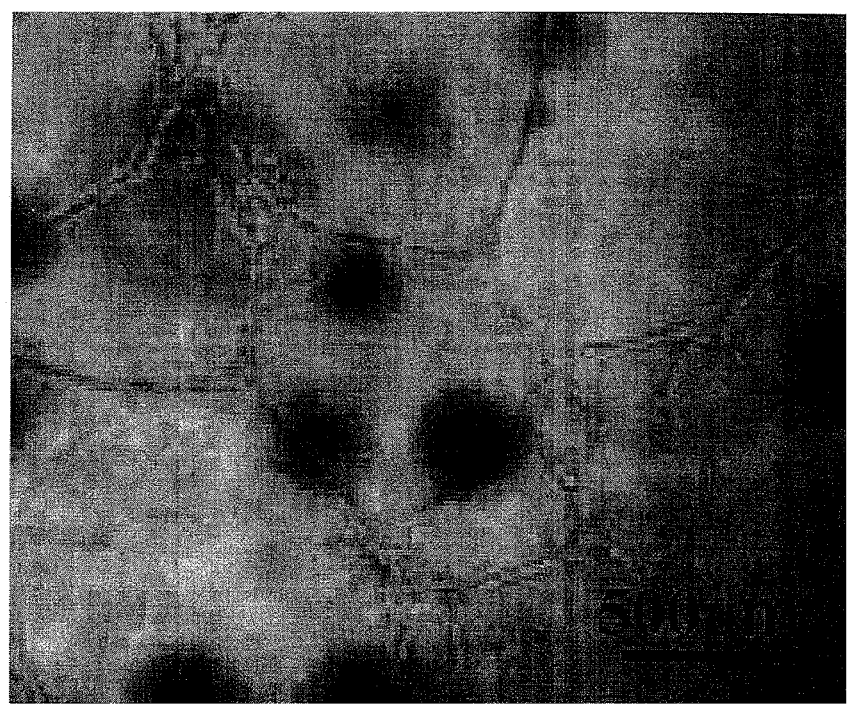
FIG. 33 is a photograph showing angiogenic potential of human dental pulp CD150$^+$ cells at the third passage of culture.

A similar experiment with human dental pulp CD150+ cell showed that the human dental pulp CD150+ cells formed an extensive networks of cords and tube-like structures, as shown in FIG. 33.

Figure 34:
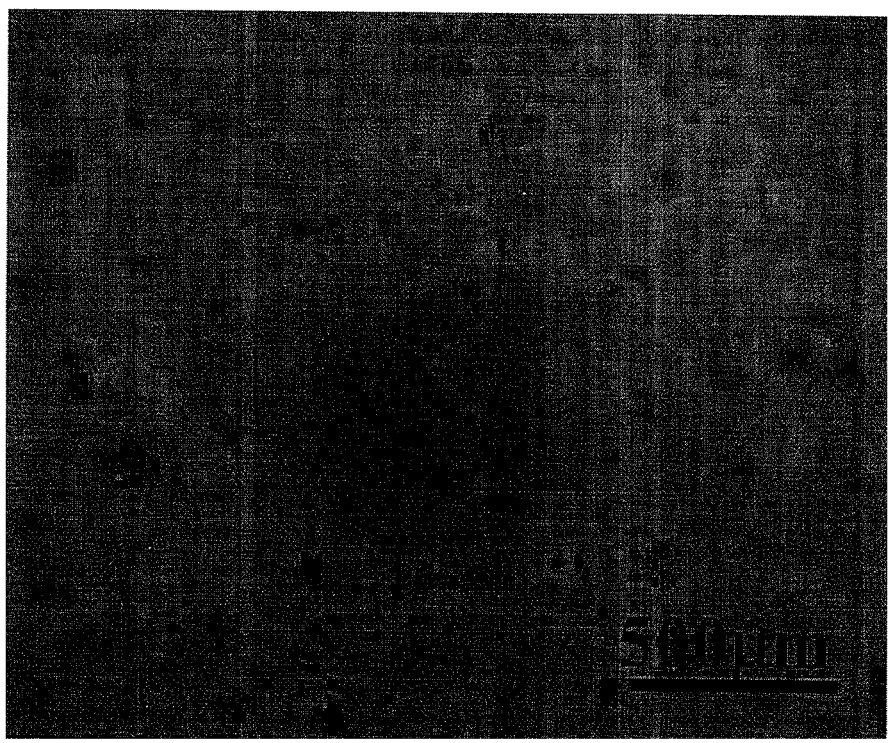
FIG. 34 is a photograph showing little angiogenic potential of human total unfractionated pulp cells at the third passage of culture.

A similar experiment with unfractionated human total pulp cells at third passage of culture showed that the unfractionated human total pulp cells did not form cords and tube-like structures, as shown in FIG. 34.

Figure 35:
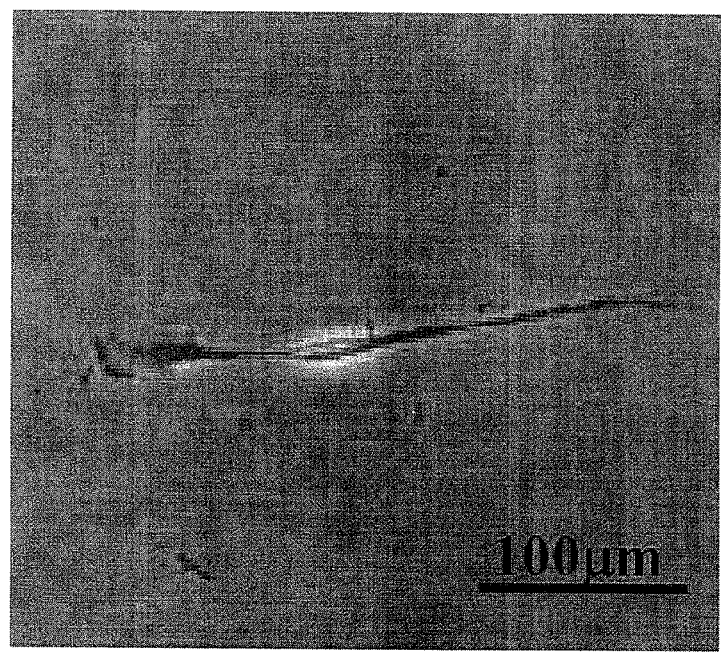
FIG. 35 is a photograph showing neurogenesis of human dental pulp CD24$^+$ cells.

On the other hand, a similar experiment with human dental pulp CD24+ cells showed that the human dental pulp CD24+ cells differentiated into nerves easily in vitro, as shown in FIG. 35.

Figure 36:
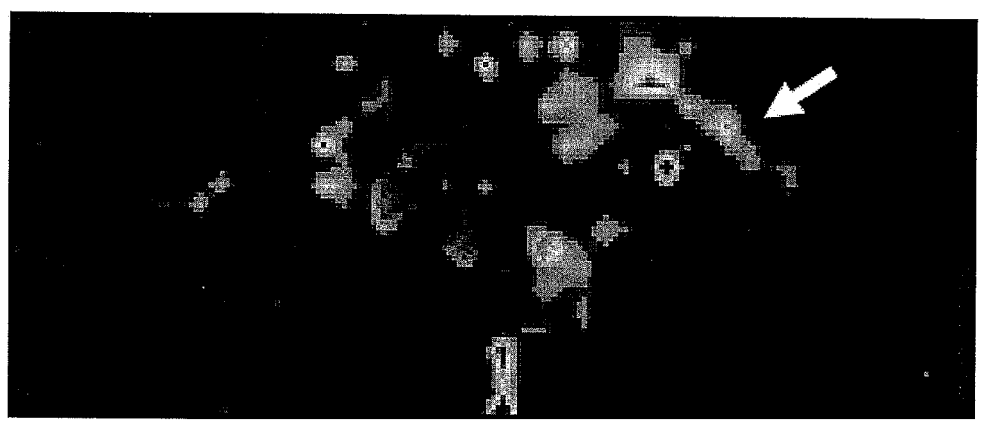
FIG. 36 is a photograph showing recovery of blood flow by laser Doppler analysis in the case of the transplantation of human dental pulp CD31$^-$/CD146$^-$ SP cells at the third passage of culture.
Figure 37:
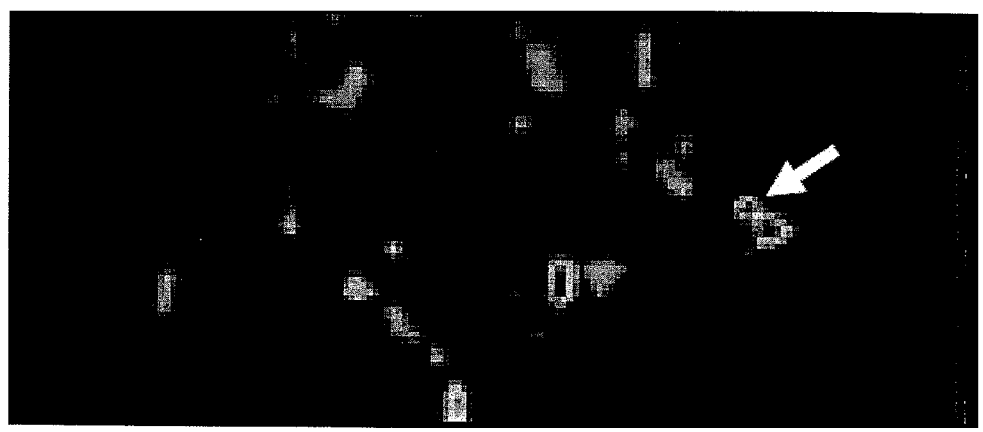
FIG. 37 is a photograph showing recovery of blood flow by laser Doppler analysis in the case of the transplantation of human dental pulp CD105$^+$ cells at the third passage of culture.
Figure 38:
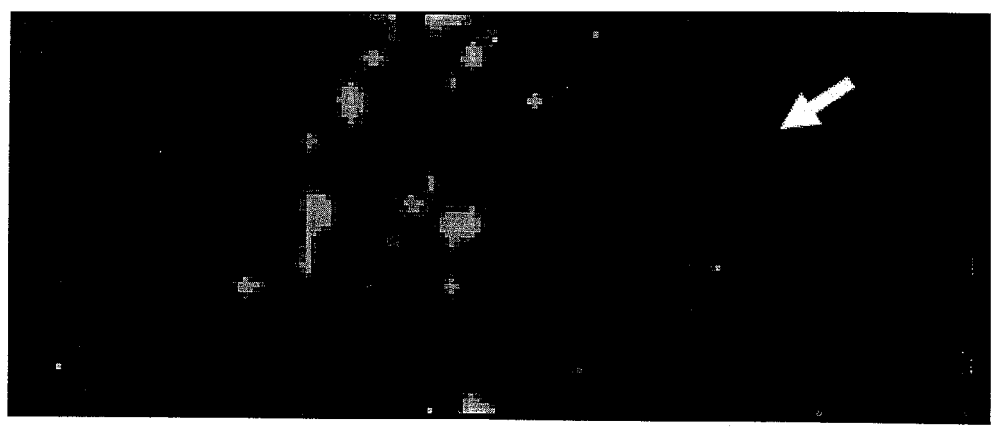
FIG. 38 is a photograph showing no recovery of blood flow by laser Doppler analysis in the case of PBS-injected control.
Figure 39:
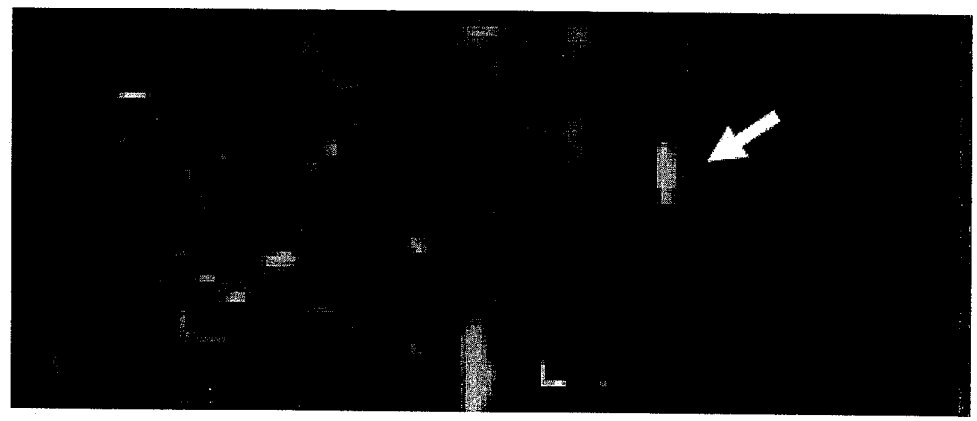
FIG. 39 is a photograph showing a little recovery of blood flow by laser Doppler analysis in the case of the transplantation of human dental pulp total pulp cells.
Figure 40:
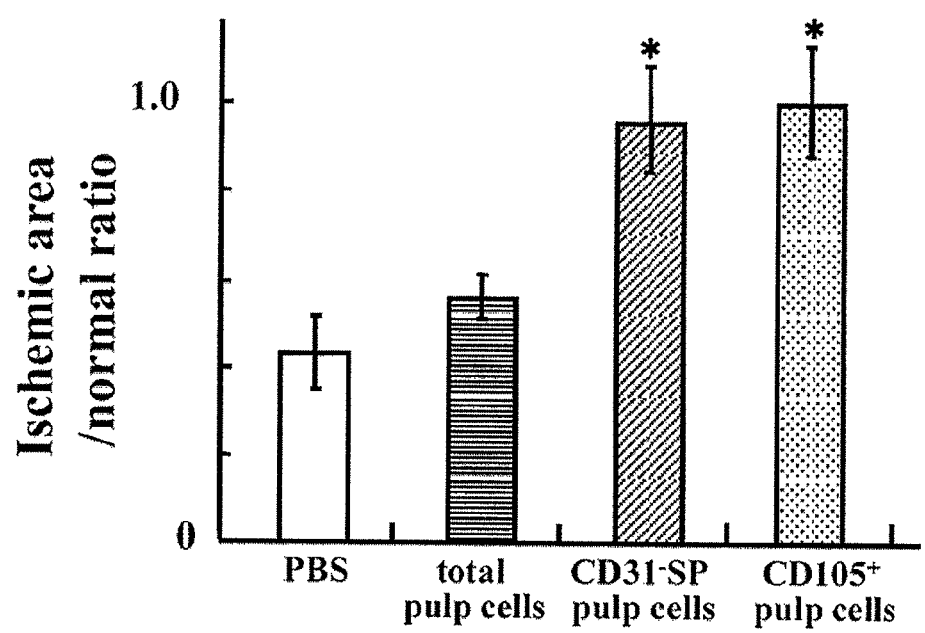
FIG. 40 is a graph showing statistical analysis of quantification of blood flow in ischemic versus control limbs obtained from five mice each in human dental pulp CD31$^-$/CD146$^-$ SP cells, human dental pulp CD105$^+$ cells and human dental pulp total pulp cells, respectively.

FIG. 36 is a photograph showing a hindlimb ischemic region with transplanted human dental pulp CD31−/CD146− SP cells at the third passage of culture. FIG. 37 is a photograph showing a hindlimb ischemic region with transplanted human dental pulp CD105+ cells at the third passage of culture. FIG. 38 is a photograph showing a hindlimb ischemic region with injected PBS control. FIG. 39 is a photograph showing a hindlimb ischemic region with transplanted human dental total pulp cells at the third passage of culture. FIGS. 36, 37, 38 and 39 show the results obtained by laser Doppler analysis, while FIG. 40 shows the cells with statistical significant difference in laser Doppler analysis. As shown in FIGS. 36, 37 and 38, transplantation of human dental pulp CD31−/CD146− SP cells or human dental pulp CD105+ cells to a hindlimb ischemic region resulted in drastic recovery of blood flow, compared to the control of PBS injection. As shown in FIG. 39, human total pulp cells at the third passage of culture showed some recovery of blood flow.

Figure 41:
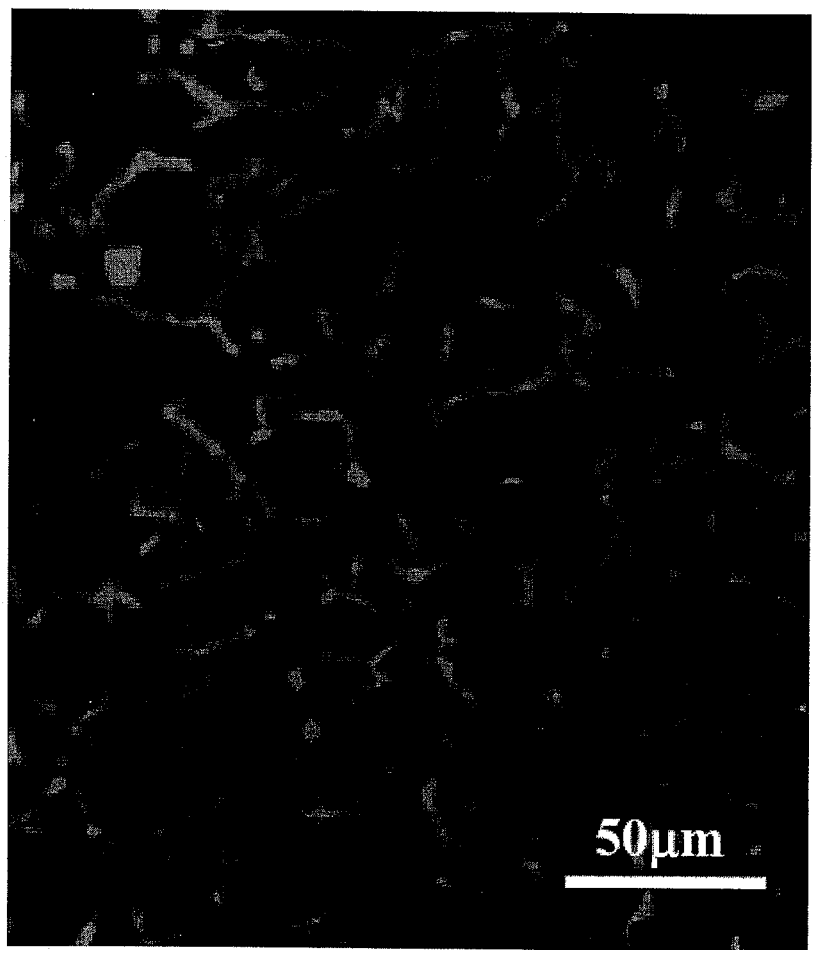
FIG. 41 is a photograph showing the vascular endothelial cells stained with BS-1 lectin 14 days after transplantation of human dental pulp CD31$^-$/CD146$^-$ SP cells.
Figure 42:
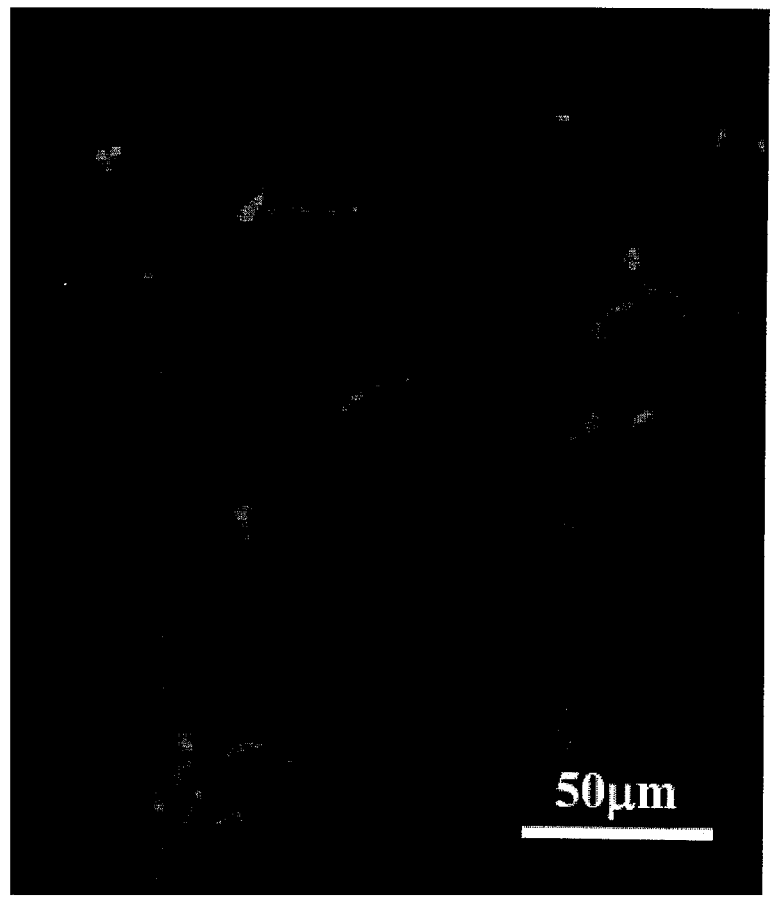
FIG. 42 is a photograph showing the vascular endothelial cells stained with BS-1 lectin 14 days after PBS-injected control.

A continuous frozen section of hindlimb ischemic region was prepared, and the density of the newly generated blood vessels was determined after the vascular endothelial cells were stained with BS-1 lectin. FIG. 41 is a photograph showing the vascular endothelial cells stained with BS-1 lectin in the case of transplantation of human dental pulp CD31−/CD146− SP cells. FIG. 42 shows a photograph showing the results in the case of the control of PBS injection, when the vascular endothelial cells were stained with BS-1 lectin. As shown clearly in FIGS. 41 and 42, the human dental pulp CD31−/CD146− SP cells accelerate vascularization drastically, compared to the control of PBS injection.

The results above indicate that the human dental pulp-derived CD31−/CD146− SP cells and the CD105+ cells are effective for both canine and porcine vasculogenesis/angiogenesis and dental pulp regeneration.

INDUSTRIAL APPLICABILITY

The dental tissue regeneration method according to the present invention, which regenerates dental tissue by inserting a root canal filler into a root canal after pulpectomy, is suitable for application of regeneration of dental pulp and recovery of dental pulp function, even if the caries is deeper with pulpitis.

DESCRIPTION OF REFERENCE CHARACTERS

100 Targeted Tooth
110 Periapical disease
200 Root Canal Filler
210 Extracellular Matrix
220 Cells Enriched For Dental Pulp Stem Cells
230 Chemotactic (Migration) Factors
300 Odontectomised Cavity In The Alveolar Bone
400 Blood Vessel
500 Dentin
610 Spongel (Gelatin)
620 Resin
630 Morphogen

The invention claimed is:

1. A dental tissue regeneration method of regenerating dental tissue in a root canal, comprising:
   pulpectomizing or enlarging and cleaning of a root canal infected with periapical disease;
   injecting an extracellular matrix containing cells enriched for dental pulp stem cells into at least an apical area of the root canal, wherein the cells enriched for dental pulp stem cells comprise CD105-positive cells, and wherein the extracellular matrix injected into at least a tooth crown-side of the apical area of the root canal also comprises granulocyte colony-stimulating factor (G-CSF).

2. The dental tissue regeneration method according to claim 1, wherein width of the root canal in the apical area is adjusted to a particular size, by enlargement of the root canal before insertion of the extracellular matrix into the apical area of the root canal.

3. The dental tissue regeneration method according to claim 1, wherein the extracellular matrix is made of a biocompatible material containing at least one of collagen, synthetic proteoglycans, gelatin, hydrogel, fibrin, phosphophorin, heparan sulfate, heparin, laminin, fibronectin, alginic acid, hyaluronic acid, chitin, PLA, PLGA, PEG, PGA, PDLLA, PCL, hydroxyapatite, β-TCP, calcium carbonate, titanium and gold.

4. The dental tissue regeneration method according to claim 1, wherein the concentration of the dental pulp stem cells in the extracellular matrix is from $1 \times 10^3$ cells/μl to $1 \times 10^6$ cells/μl.

5. A dental tissue regeneration method of regenerating dental tissue in root canal, comprising:
   pulpectomizing or enlarging and cleaning of a root canal infected with periapical disease; and
   injecting an extracellular matrix containing cells enriched for dental pulp stem cells into at least an apical area of the root canal, wherein the cells enriched for dental pulp stem cells comprise CD31-negative/CD146-negative cells, and wherein the extracellular matrix injected into at least a tooth crown-side of the apical area of the root canal also comprises stromal cell-derived factor 1 (SDF1).

6. The dental tissue regeneration method according to claim 5, wherein width of the root canal in the apical area is adjusted to a particular size, by enlargement of the root canal before insertion of the extracellular matrix into the apical area of the root canal.

7. The dental tissue regeneration method according to claim 5, wherein the extracellular matrix is made of a biocompatible material containing at least one of collagen, synthetic proteoglycans, gelatin, hydrogel, fibrin, phosphophorin, heparan sulfate, heparin, laminin, fibronectin, alginic acid, hyaluronic acid, chitin, PLA, PLGA, PEG, PGA, PDLLA, PCL, hydroxyapatite, 62-TCP, calcium carbonate, titanium and gold.

8. The dental tissue regeneration method according to claim 5, wherein the concentration of the dental pulp stem cells in the extracellular matrix is from $1\times10^3$ cells/µl to $1\times10^6$ cells/µl.

* * * * *

UNITED STATES PATENT AND TRADEMARK OFFICE
CERTIFICATE OF CORRECTION

PATENT NO. : 8,920,791 B2  
APPLICATION NO. : 12/922097  
DATED : December 30, 2014  
INVENTOR(S) : Misako Nakashima Page 1 of 2

It is certified that error appears in the above-identified patent and that said Letters Patent is hereby corrected as shown below:

Title Page

In column 2 (page 1, item 56) at line 25, Under Other Publications, change "Hydroxyapatitie" to --Hydroxyapatite--.

In column 2 (page 1, item 56) at line 26, Under Other Publications, change "Wonds" to --Wounds--.

In column 2 (page 1, item 56) at line 36, Under Other Publications, change "differenct" to --different--.

In column 2 (page 1, item 56) at line 47, Under Other Publications, change "Labrary" to --Library--.

In column 1 (page 2, item 56) at line 5, Under Other Publications, change "Jounal" to --Journal--.

In column 2 (page 2, item 56) at lines 9-10, Under Other Publications, change "regenartion"," to --regeneration",--.

In column 2 (page 2, item 56) at line 18, Under Other Publications, change "pithelial" to --epithelial--.

In the Specification

In column 8 at line 48, Change "potental" to --potential--.

In column 8 at line 55, Change "potental." to --potential.--.

In column 8 at line 57, Change "potental" to --potential--.

In column 8 at line 59, Change "potental" to --potential--.

In column 8 at line 61, Change "potental" to --potential--.

In column 9 at line 40, Change "it" to --It--.

In column 11 at line 28, Change "CD146$^+$SP" to --CD146$^+$ SP--.

Signed and Sealed this  
Twentieth Day of October, 2015

Michelle K. Lee  
*Director of the United States Patent and Trademark Office*

In column 11 at line 1 (Table 1), Change "CD146⁻SP" to --CD146⁻ SP--.

In column 11 at line 1 (Table 1), Change "CD31⁺SP" to --CD31⁺ SP--.

In column 11 at line 1 (Table 2), Change "CD31⁻SP" to --CD31⁻ SP--.

In column 11 at line 1 (Table 2), Change "CD31⁺SP" to --CD31⁺ SP--.

In column 12 at line 46, Change "CD31⁺SP" to --CD31⁺ SP--.

In column 14 at line 10, Change "CD31⁺SP" to --CD31⁺ SP--.

In column 14 at line 17, Change "—one" to --one--.

In columns 15-16 at line 11 (Table 4), Change "CD 105" to --CD105--.

In the Claims

In column 18 at line 66, In Claim 7, change "62" to --β--.